US012690842B2

(12) United States Patent
Driver et al.

(10) Patent No.: US 12,690,842 B2
(45) Date of Patent: Jul. 28, 2026

(54) ULTRASOUND PROBE WITH MONOLITHIC THERMOPLASTIC BODY

(71) Applicant: Profound Medical Inc., Mississauga (CA)

(72) Inventors: Christopher Driver, Oakville (CA); Samantha Lee, Mississauga (CA); Nicholas Alexander Lavdas, London (CA)

(73) Assignee: Profound Medical Inc., Mississauga (CA)

( * ) Notice: Subject to any disclaimer, the term of this patent is extended or adjusted under 35 U.S.C. 154(b) by 187 days.

(21) Appl. No.: 18/632,859

(22) Filed: Apr. 11, 2024

(65) Prior Publication Data

US 2025/0318803 A1     Oct. 16, 2025

(51) Int. Cl.
*A61B 8/00* (2006.01)
*A61B 8/12* (2006.01)
(52) U.S. Cl.
CPC ................ *A61B 8/445* (2013.01); *A61B 8/12* (2013.01); *A61B 8/4281* (2013.01); *A61B 8/546* (2013.01)
(58) Field of Classification Search
CPC ......... A61B 8/445; A61B 8/12; A61B 8/4281; A61B 8/546; A61B 8/488; A61B 8/085; A61B 8/0891; A61B 8/4483; A61B 8/4494; A61N 2007/0043; A61N 7/022
See application file for complete search history.

(56) References Cited

U.S. PATENT DOCUMENTS

| | | | |
|---|---|---|---|
| 4,326,418 | A | 4/1982 | Pell, Jr. |
| 4,880,011 | A | 11/1989 | Imade et al. |
| 5,295,484 | A | 3/1994 | Marcus et al. |
| 5,593,381 | A | 1/1997 | Tannenbaum et al. |
| 5,593,415 | A | 1/1997 | Adrian |

(Continued)

FOREIGN PATENT DOCUMENTS

| | | | |
|---|---|---|---|
| EP | 3950036 A1 | 2/2022 | |
| EP | 4110189 A1 | 1/2023 | |

(Continued)

OTHER PUBLICATIONS

International Search Report for PCT App. No. PCT/CA2025/050514, dated Aug. 18, 2025.

(Continued)

*Primary Examiner* — Joel Lamprecht
(74) *Attorney, Agent, or Firm* — Intrinsic Law Corp.

(57) ABSTRACT

An ultrasound probe includes a shaft including a monolithic thermoplastic body having an outer wall that defines a diameter of the shaft, the monolithic thermoplastic body defining a plurality of channels that extend from a proximal end of the shaft. The plurality of channels includes an ultrasound transducer channel and a cooling channel. A tip is located at a distal end of the shaft and is formed by the monolithic thermoplastic body. A printed circuit board (PCB) including at least one ultrasound transducer element is disposed in the ultrasound transducer channel. The outer wall can define an acoustic window that is aligned with the at least one ultrasound transducer elements Alternatively, a hole can be defined in the outer wall and the hole can be covered with another material or a balloon to define the acoustic window.

14 Claims, 23 Drawing Sheets

(56) References Cited

U.S. PATENT DOCUMENTS

| | | | |
|---|---|---|---|
| 5,601,526 | A | 2/1997 | Chapelon et al. |
| 5,620,479 | A | 4/1997 | Diederich |
| 5,647,361 | A | 7/1997 | Damadian |
| 5,666,954 | A | 9/1997 | Chapelon et al. |
| 5,733,315 | A | 3/1998 | Burdette et al. |
| 6,007,257 | A | 12/1999 | Ogawa et al. |
| 6,050,943 | A | 4/2000 | Stayton et al. |
| 6,100,626 | A | 8/2000 | Frey et al. |
| 6,113,546 | A | 9/2000 | Suorsa et al. |
| 6,122,551 | A | 9/2000 | Rudie et al. |
| 6,241,725 | B1 | 6/2001 | Cosman |
| 6,254,553 | B1 | 7/2001 | Lidgren et al. |
| 6,379,320 | B1 | 4/2002 | Lafon et al. |
| 6,393,314 | B1 | 5/2002 | Watkins et al. |
| 6,418,337 | B1 | 7/2002 | Torchia et al. |
| 6,432,067 | B1 | 8/2002 | Martin et al. |
| 6,490,488 | B1 | 12/2002 | Rudie et al. |
| 6,500,121 | B1 | 12/2002 | Stayton et al. |
| 6,516,211 | B1 | 2/2003 | Acker et al. |
| 6,522,142 | B1 | 2/2003 | Freundlich |
| 6,537,306 | B1 | 3/2003 | Burdette et al. |
| 6,542,767 | B1 | 4/2003 | McNichols et al. |
| 6,559,644 | B2 | 5/2003 | Freundlich et al. |
| 6,582,381 | B1 | 6/2003 | Yehezkeli et al. |
| 6,589,174 | B1 | 7/2003 | Chopra et al. |
| 6,618,608 | B1 | 9/2003 | Watkins et al. |
| 6,618,620 | B1 | 9/2003 | Freundlich et al. |
| 6,623,430 | B1 | 9/2003 | Stayton et al. |
| 6,671,535 | B1 | 12/2003 | McNichols et al. |
| 6,692,450 | B1 | 2/2004 | Coleman |
| 6,692,518 | B2 | 2/2004 | Carson |
| 6,735,461 | B2 | 5/2004 | Vitek et al. |
| 6,746,465 | B2 | 6/2004 | Diederich et al. |
| 6,755,849 | B1 | 6/2004 | Gowda et al. |
| 6,818,012 | B2 | 11/2004 | Ellingboe |
| 6,823,216 | B1 | 11/2004 | Salomir et al. |
| 7,044,960 | B2 | 5/2006 | Voorhees et al. |
| 7,135,029 | B2 | 11/2006 | Makin et al. |
| 7,167,741 | B2 | 1/2007 | Torchia et al. |
| 7,229,411 | B2 | 6/2007 | Stayton et al. |
| 7,233,820 | B2 | 6/2007 | Gilboa |
| 7,344,529 | B2 | 3/2008 | Torchia et al. |
| 7,404,809 | B2 | 7/2008 | Susi |
| 7,473,224 | B2 | 1/2009 | Makin |
| 7,771,418 | B2 | 8/2010 | Chopra et al. |
| 7,806,892 | B2 | 10/2010 | Makin et al. |
| 7,951,182 | B2 | 5/2011 | Stelea et al. |
| 7,993,289 | B2 | 8/2011 | Quistgaard et al. |
| 8,021,406 | B2 | 9/2011 | Cazzini et al. |
| 8,025,688 | B2 | 9/2011 | Diederich et al. |
| 8,066,641 | B2 | 11/2011 | Barthe et al. |
| 8,244,327 | B2 | 8/2012 | Fichtinger et al. |
| 9,707,413 | B2 | 7/2017 | Chopra et al. |
| 12,458,778 | B2 * | 11/2025 | Hamm ............. A61M 25/0108 |
| 2001/0003798 | A1 | 6/2001 | McGovern et al. |
| 2003/0004439 | A1 | 1/2003 | Pant et al. |
| 2003/0018266 | A1 | 1/2003 | Makin et al. |
| 2003/0069502 | A1 | 4/2003 | Makin et al. |
| 2003/0092988 | A1 | 5/2003 | Makin |
| 2006/0206105 | A1 | 9/2006 | Chopra et al. |
| 2006/0241368 | A1 | 10/2006 | Fichtinger et al. |
| 2006/0241442 | A1 | 10/2006 | Barthe et al. |
| 2007/0021648 | A1 | 1/2007 | Lenker et al. |
| 2007/0106157 | A1 | 5/2007 | Kaczkowski et al. |
| 2007/0239062 | A1 | 10/2007 | Chopra et al. |
| 2008/0242970 | A1 | 10/2008 | Minagawa et al. |
| 2009/0143775 | A1 | 6/2009 | Rizoiu et al. |
| 2009/0171185 | A1 | 7/2009 | Chou et al. |
| 2010/0256480 | A1 | 10/2010 | Bottomley et al. |
| 2011/0034833 | A1 | 2/2011 | Chopra et al. |
| 2011/0144524 | A1 | 6/2011 | Fish et al. |
| 2011/0282156 | A1 | 11/2011 | Lenker et al. |
| 2014/0163382 | A1 | 6/2014 | Gubbini et al. |
| 2018/0263651 | A1 * | 9/2018 | Hissong ................. A61B 34/20 |
| 2020/0178941 | A1 * | 6/2020 | Thiagarajan ......... G01N 29/326 |
| 2023/0218263 | A1 | 7/2023 | Barrish et al. |

FOREIGN PATENT DOCUMENTS

| | | | | |
|---|---|---|---|---|
| KR | 20130029042 A | * | 3/2013 | .............. A61B 8/12 |
| WO | WO2011045695 A1 | | 4/2011 | |
| WO | WO2011091847 A1 | | 8/2011 | |

OTHER PUBLICATIONS

Chopra et al., Med. Phys., 27(6): 1281-1286, 2000.
Chopra et al., IEEE Transactions on Ultrasonics, Ferroelectrics, and Frequency Control, 50(7):881-889, 2003.
Diederich et al., Med. Phys., 31(2):405-413, 2004.
Kowalski et al., Phys. Med. Biol., 48:633-651, 2003.
Lafon et al., Ultrasonics, 36:683-687, 1998.
Lafon et al., Ultrasound Med. Biol., 30(1):113-122, 2004.
McNichols et al., Lasers Surg. Med., 34:48-55, 2004.
Ross et al., Phys. Med. Biol., 49:189-204, 2004.
Smith et al., Int. J. Hyperthermia, 17(3):271-282, 2001.
Vanne et al., Phys. Med. Biol., 48: 31-43, 2003.
H. L. Liu et al., "Pilot point temperature regulation for thermal lesion control during ultrasound thermal therapy", Med. Biol. Eng. Comput., 2004, p. 178-188, vol. 42.
M. Burtnyk et al., "Quantitative analysis of 3-D conformal MRI-guided transurethral ultrasound therapy of the prostate: Theoretical simulations", International Journal of Hyperthermia, Mar. 2009, p. 116-131, vol. 25, No. 2.
European Patent Office, "Extended European Search Report—Application No. 12835517.9", Oct. 27, 2015, EPO.

* cited by examiner

ULTRASOUND PROBE WITH MONOLITHIC THERMOPLASTIC BODY

TECHNICAL FIELD

This application relates generally to ultrasound therapy devices.

BACKGROUND

Ultrasound therapy devices are used to treat various conditions such as cancer, enlarged prostates (benign prostatic hyperplasia) and kidney stones. Current ultrasound therapy devices are formed out of metal, which makes then difficult and/or expensive to customize.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages, and novel features of the disclosure will be set forth in the following detailed description of the disclosure when considered in conjunction with the drawings, which are intended to illustrate, not limit, the invention.

An aspect of the invention is directed to an ultrasound probe comprising a shaft including a monolithic thermoplastic body having an outer wall that defines a diameter of the shaft, the monolithic thermoplastic body defining a plurality of channels that extend from a proximal end of the shaft, the plurality of channels including: an ultrasound transducer channel, and a cooling channel; a tip disposed at a distal end of the shaft; and a printed circuit board (PCB) including at least one ultrasound transducer element electrically connected to the printed circuit board, the PCB disposed in the ultrasound transducer channel, wherein the outer wall defines an acoustic window that is aligned with the at least one ultrasound transducer element.

In one or more embodiments, the outer wall has a tapered thickness at the acoustic window. In one or more embodiments the acoustic window is aligned with a first axis that is orthogonal to a major plane of the printed circuit board, a thickness of the outer wall at a location that passes through the first axis is smaller than a thickness of the outer wall at a location that passes through a second axis that passes through the PCB and that is orthogonal to the major plane, a width of the PCB is measured with respect to the second axis, and a length of the PCB is measured with respect to a third axis that is orthogonal to the first and second axes.

In one or more embodiments the ultrasound transducer channel includes a rectangular portion configured to secure the PCB and a rounded portion to receive an ultrasound coupling fluid. In one or more embodiments the tip has a tip angle defined by a tip axis that passes through an opening of the tip and a central axis of the shaft, the central axis orthogonal to the diameter of the shaft and parallel to a length of the shaft, the tip angle greater than equal to 120 degrees and less than or equal to 150 degrees.

In one or more embodiments the plurality of channels includes a guidewire channel that extends from the proximal end of the shaft to the tip, the guidewire channel connected to an opening defined at distal end of the tip, the guidewire channel and the opening configured to receive a guidewire. In one or more embodiments the plurality of channels includes a bodily fluids channel that extends from the proximal end of the shaft to the tip, the bodily fluids channel connected to an opening defined at a distal end of the tip, the bodily fluids channel and the opening configured to receive bodily fluids from the patient. In one or more embodiments the plurality of channels includes an ultrasound coupling fluid channel having a distal end that is fluidly coupled to the ultrasound transducer channel to allow an ultrasound coupling fluid to circulate between the ultrasound coupling fluid channel and the ultrasound transducer channel. In one or more embodiments the monolithic thermoplastic body includes the tip.

In one or more embodiments the plurality of channels includes a tool channel configured to receive a medical instrument. In one or more embodiments the plurality of channels includes a drug delivery channel configured to introduce a drug to a target location.

Another aspect of the invention is directed to an ultrasound probe comprising a shaft including a monolithic thermoplastic body having an outer wall that defines a diameter of the shaft, the monolithic thermoplastic body defining a plurality of channels that extend from a proximal end of the shaft, the plurality of channels including: an ultrasound transducer channel, and a cooling channel; a tip disposed at a distal end of the shaft; a printed circuit board (PCB) including at least one ultrasound transducer element electrically connected to the printed circuit board, the PCB disposed in the ultrasound transducer channel, wherein the outer wall defines a hole that is aligned with and that extends along the at least one ultrasound transducer element; and a section of material covering the hole to form an acoustic window, the section of material attached to the monolithic thermoplastic body to form a fluid seal between the section of material and the monolithic thermoplastic body.

In one or more embodiments the monolithic thermoplastic body and the section of material are formed of the same material. In one or more embodiments a thickness of the section of material is less than a thickness of the outer wall.

Another aspect of the invention is directed to an ultrasound probe comprising a shaft including a monolithic thermoplastic body having an outer wall that defines a diameter of the shaft, the monolithic thermoplastic body defining a plurality of channels that extend from a proximal end of the shaft, the plurality of channels including: an ultrasound transducer channel, and a cooling channel; a tip disposed at a distal end of the shaft; a printed circuit board (PCB) including at least one ultrasound transducer element electrically connected to the printed circuit board, the PCB disposed in the ultrasound transducer channel, wherein the outer wall defines a hole that is aligned with and that extends along the at least one ultrasound transducer element; and a balloon covering the hole to form an acoustic window, the balloon having a wall and first and second ends, the first and second ends attached to the monolithic thermoplastic body to form a fluid seal between the first and second ends and the monolithic thermoplastic body.

In one or more embodiments the balloon is configured to inflate and deflate in response to a pressure applied by an ultrasonic coupling fluid in the ultrasound transducer channel. In one or more embodiments the wall of the balloon has a uniform thickness such that the balloon is configured to expand symmetrically in an inflated state. In one or more embodiments the wall on a first side of the balloon is thinner than the wall on a second side of the balloon such that the balloon is configured to expand asymmetrically towards the first side. In one or more embodiments the second side covers the hole to form the acoustic window.

In one or more embodiments the balloon is a first balloon, the first balloon attached to a first side of the monolithic thermoplastic body, the ultrasound probe further comprises a second balloon attached to a second side of the monolithic thermoplastic body, and the plurality of channels includes a fluid channel that is fluidly coupled to the second balloon through a conduit defined in the outer wall on the second side of the monolithic thermoplastic body, the fluid channel supplying a fluid to set an inflation state of the second balloon.

In one or more embodiments, the ultrasound probe further comprises a material overmolded onto the tip, the material having a lower coefficient of friction than an external surface of the tip. In one or more embodiments, a proximal portion of the monolithic thermoplastic body has a larger diameter than a distal portion of the monolithic thermoplastic body. In one or more embodiments, a coating is disposed on the balloon, the coating including a material to be introduced during an ultrasound ablation procedure.

BRIEF DESCRIPTION OF THE DRAWINGS

For a fuller understanding of the nature and advantages of the concepts disclosed herein, reference is made to the detailed description of preferred embodiments and the accompanying drawings.

DETAILED DESCRIPTION

An ultrasound therapy device includes a shaft and a tip that are formed of a monolithic thermoplastic body. The monolithic thermoplastic body can be formed by injection molding or another process. A plurality of channels are defined in the shaft, each channel extending from a proximal end of the shaft. The plurality of channels includes at least an ultrasound transducer channel and a cooling channel. The ultrasound transducer channel is configured to receive one or more ultrasound transducer elements that is/are mounted on an elongated printed circuit board (PCB). The cooling channel is configured to receive a cooling fluid to cool the shaft including the one or more ultrasound transducer elements during operation.

The shaft includes an ultrasound window that is aligned with the one or more ultrasound transducer elements such that ultrasound energy produced by the one or more ultrasound transducer elements passes through the ultrasound window. In one embodiment, the ultrasound window can be defined by a tapered or narrowed region of an outer wall of the monolithic thermoplastic body.

In other embodiments, a hole is defined in the outer wall of the monolithic thermoplastic body. The hole is sized to correspond to a length and a width of the ultrasound window. A section of material can be attached, adhered, or thermoplastically welded to the monolithic thermoplastic body over the hole. The section of material can function as the acoustic window. Alternatively, a balloon can be attached or adhered to the monolithic thermoplastic body over the hole. The balloon can function as the acoustic window. The balloon can be configured to inflate symmetrically or asymmetrically in response to pressure applied by ultrasound coupling fluid in the ultrasound transducer channel.

Figure 1:
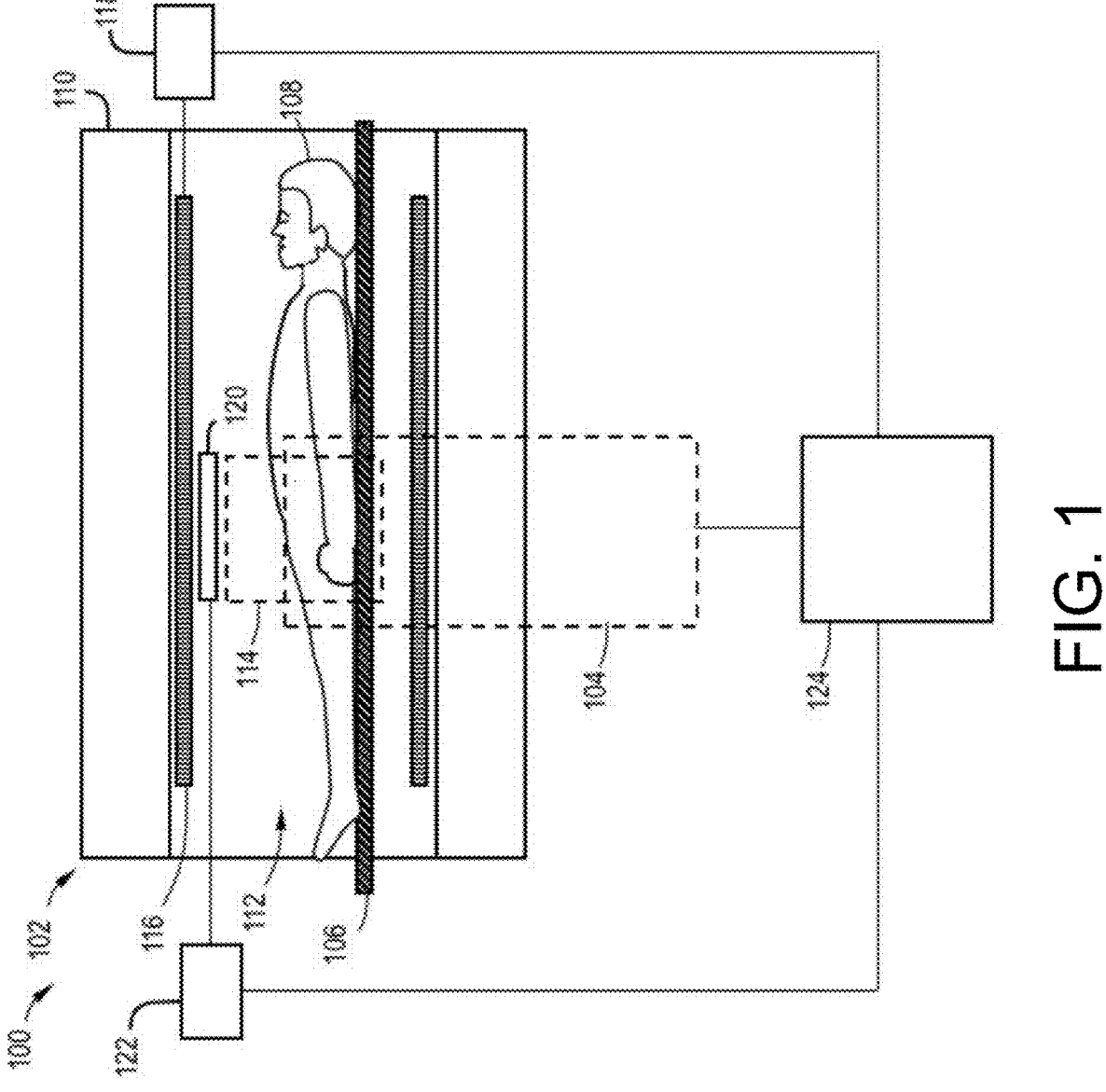
FIG. 1 is a diagram of a medical system in which at least some of the apparatus, systems, and/or methods disclosed herein are employed.

FIG. 1 is a diagram of a medical system 100 in which at least some of the apparatus, systems, and/or methods disclosed herein are employed, in accordance with at least some embodiments. The system 100 includes a patient support 106 (on which a patient 108 is shown), a magnetic resonance system 102 and an image-guided energy delivery system 104.

The magnetic resonance system 102 includes a magnet 110 disposed about an opening 112, an imaging zone 114 in which the magnetic field is strong and uniform enough to perform magnetic resonance imaging (MRI), a set of magnetic field gradient coils 116 to change the magnetic field rapidly to enable the spatial coding of MRI signals, a magnetic field gradient coil power supply 118 that supplies current to the magnetic field gradient coils 116 and is controlled as a function of time, a transmit/receive coil 120

(also known as a "body" coil) to manipulate the orientations of magnetic spins within the imaging zone 114, a radio frequency transceiver 122 connected to the transmit/receive coil 120, and a computer 124, which performs tasks (by executing instructions and/or otherwise) to facilitate operation of the MRI system 102 and is coupled to the radio frequency transceiver 122, the magnetic field gradient coil power supply 118, and the image-guided energy delivery system 104. The image-guided energy delivery system 104 includes a therapeutic applicator, such as an ultrasound applicator, to perform image-guided therapy (e.g., thermal therapy) to treat a treatment volume in the patient 108.

The MRI computer 124 can include more than one computer in some embodiments, at least one of which can be dedicated to the MRI system 102. In at least some embodiments, the MRI computer 124 and/or one or more other computing devices (not shown) in and/or coupled to the system 100 may also perform one or more tasks (by executing instructions and/or otherwise) such as to control the driving or operating frequency of the ultrasound elements in the therapeutic applicator, such as at the center frequency $(f_0)$ and/or at a higher harmonic $(3f_0)$ of the center frequency.

One or more of the computers, including computer 124, can include a treatment plan for and/or program instructions for determining a treatment plan (e.g., in real time) for the patient 108 that includes the target treatment volume and the desired or minimal energy (e.g., thermal) dose for the target treatment volume. The treatment plan can also include the desired operating or driving frequency of the ultrasound elements, such as $f_0$ and/or $3f_0$. The computer(s) can use images from the magnetic resonance system 102 to image guide the rotational position and insertion-retraction position of the therapeutic applicator. In some embodiments, one or more dedicated computers control the image-guided energy delivery system 104. Some or all of the foregoing computers can be in communication with one another (e.g., over a local area network, a wide area network, a cellular network, a WiFi network, or other network), for example through a software-controlled link to a communication network.

In some embodiments, the treatment plan includes a set of initial parameters for driving each ultrasound element such as its initial frequency, initial phase, and initial amplitude. These parameters can be updated in real time based on the measured temperature of the target volume, for example as determined by MR thermometry.

In other embodiments, the image-guided energy delivery system 104 can be guided with another imaging device, such as an ultrasound imaging device. In other embodiments, the image-guided energy delivery system 104 can be used without an imaging device in which case the image-guided energy delivery system 104 is an energy delivery system 104.

Figure 2:
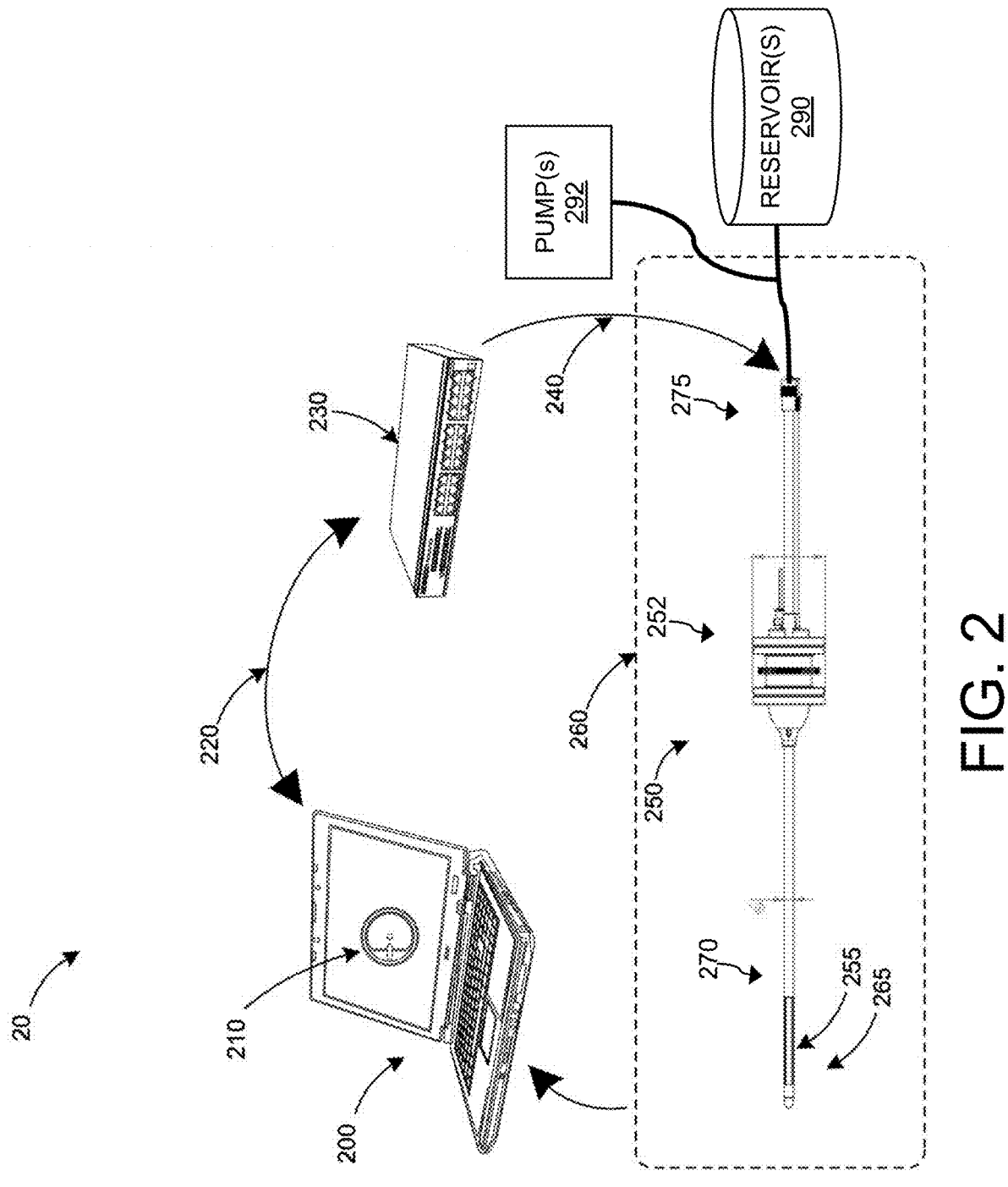
FIG. 2 is a simplified illustration of an example image-guided energy delivery system according to one or more embodiments.

FIG. 2 is a simplified illustration of an example image-guided energy delivery system 20 according to one or more embodiments. The image-guided energy delivery system 20 can be the same as or different than image-guided energy delivery system 104. The system 20 includes a primary computer 200, such as a portable PC, workstation, or other processing device having a processor, memory, and coupled to some input/output apparatus. The primary computer 200 may include a display and may support a user interface 210, such as a graphical user interface, to facilitate control of and/or observation of the thermal therapy treatment process.

The primary computer 200 is adapted for coupling to other systems and components through a computer interface connection 220. Connection 220 carries data and information to and from the primary computer 200 and may comprise standard or special-purpose electrical wiring connection cables, such as serial connection cables or the like. Also, connection 220 may be achieved wirelessly (e.g., via Bluetooth, WiFi, cellular, or other wireless connection), and may further be achieved by way of multiple connections, over a network, or by another suitable method.

The primary computer 200 is coupled through connection 220 to a power controller 230. The power controller 230 may be implemented as a stand-alone hardware apparatus but may be implemented as a part of the primary computer 200, e.g., by being built onto a special card in a computer or server system that accommodates such hardware components. In addition, at least some of the functionality of the power controller 230 can be achieved in software that can run on the primary computer 200 or another computer.

The power controller 230 may include at least a processor that processes machine or program instructions, which may be provided to the processor from another component of system 20 and/or may be stored on a memory device in the power controller 230. Circuitry including analog and/or digital circuitry may be included within the power controller 230 so as to determine an output power to one or more ultrasound therapy transducer elements in an ultrasound therapy apparatus 250.

In some embodiments, the power controller 230 may deliver controlled electrical driving signals to a plurality of ultrasound transducer elements (e.g., PZT array elements) in ultrasound therapy apparatus 250. The driving signals may be controlled to deliver a programmed amount of power to each element or to groups of elements of therapy apparatus 250. The driving signals may also be controlled so as to provide a determined driving voltage, current, amplitude, waveform, relative phase, and/or frequency (e.g., $f_0$ and/or $3f_0$) to the ultrasonic transducers of therapy apparatus 250. Such electrical driving signals are carried from the power controller 230 to the ultrasound therapy apparatus 250 over suitable wires, cables, or buses 240. Appropriate plug interfaces or connectors may be included so as to mate the various ends of the connectors or buses to and from their associated components.

The ultrasound therapy apparatus 250 includes an ultrasound array 255 disposed in a shaft 270 at a distal portion 265 that is inserted into a portion of a patient's body (e.g., urethra) to deliver a suitable dose of ultrasound energy to tissue in a diseased region of the patient's body. A proximal end 275 of the ultrasound therapy apparatus 250 remains outside of the patient's body while the ultrasound energy is delivered. The ultrasound therapy apparatus 250 can include a handle 252 that can be rotated to change the angular orientation of the ultrasound array 255 within the patient's body. The ultrasound energy produced by the ultrasound array 255 can also be electronically focused or directed by modifying the relative phase of some or all of the ultrasound elements in the ultrasound array 255. The ultrasound array 255 includes one or more (e.g., at least one) ultrasound transducer elements.

The ultrasound therapy apparatus 250 including the shaft 270 includes a plurality of channels defined therein. The ultrasound array 255 can be disposed in one of the channels. One or more of the channels can be fluidly coupled to one or more reservoirs 290 to supply and/or circulate fluids (e.g., liquids and/or gasses) to/within the ultrasound therapy apparatus 250. Examples of such fluids include an ultrasound coupling fluid, a cooling fluid, saline, and/or other fluids. One or more pumps 292 can be fluidly coupled to one or more of the channels, for example to circulate one or more fluids (e.g., ultrasound coupling fluid, cooling fluid, and/or another fluid), to inflate/deflate balloon(s) attached to the shaft, to provide other pumping means.

The patient and the ultrasound therapy apparatus 250 are generally disposed in an imaging volume 260 such as within an MRI apparatus, which can provide (e.g., via MRI computer 124) real-time images of the relevant parts of the patient (e.g., the treatment volume) to the primary computer 200 or display and user interface 210. The imaging volume 260 can be the same as (or a portion of) the imaging zone 114. In some embodiments, real-time monitoring of the thermal therapy is performed so that a clinical operator can monitor the progress of the therapy within the treatment volume or diseased tissue. Manual or automated changes can be made to the power signals from the power controller 230 based on input from the results and progress of the treatment.

The feedback and coupling of the treatment system components to the control components in system 20 can be used to ensure that an optimum radio frequency (RF) power signal, including the optimal operating or driving frequency and/or relative phase is provided to each element of the ultrasound array 255 used in treatment of diseased tissues. Some examples include treatment of prostate cancer tumors in male patients using MRI guided ultrasound therapy applications.

The power controller 230 may include separate circuit cards having individual processors, amplifiers, filters and other components to achieve the desired driving power output to the elements of ultrasound array 255 of ultrasound treatment apparatus 250. Alternatively, a single processor may be employed to control the behavior of the various power channels to each array element.

Figure 3:
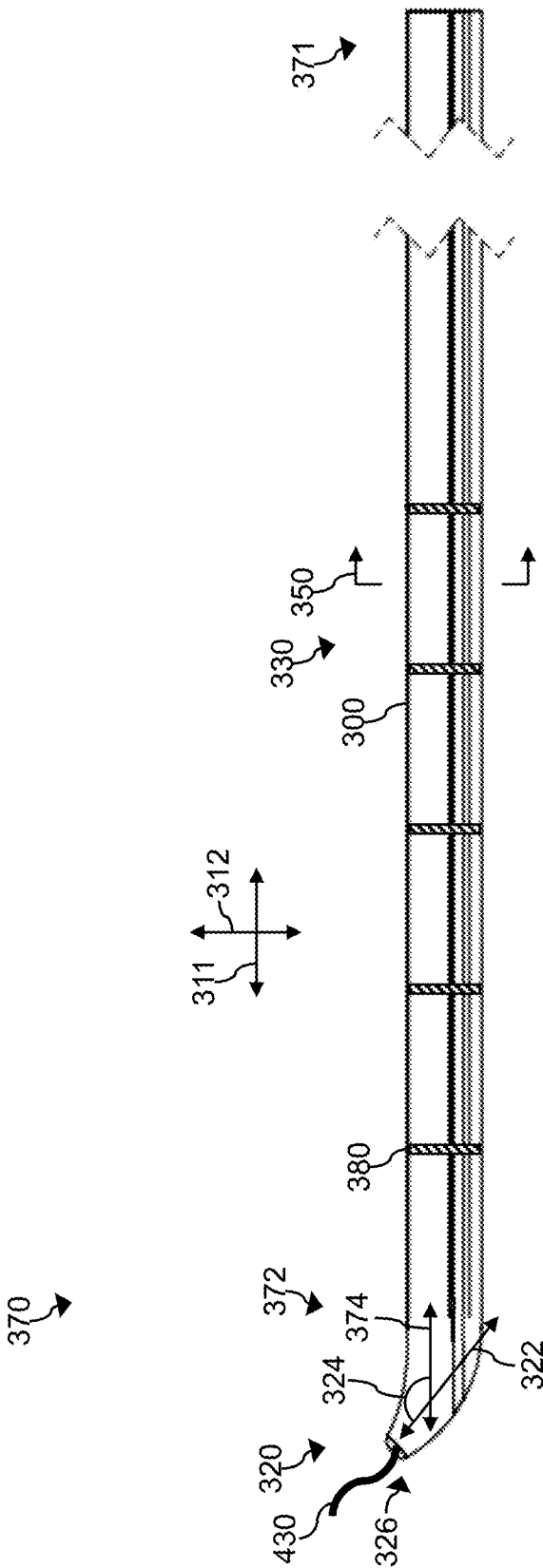
FIG. 3 is a side view of a shaft for an ultrasound therapy apparatus according to an embodiment.

FIG. 3 is a side view of a shaft 370 for an ultrasound therapy apparatus according to an embodiment. The ultrasound therapy apparatus can alternately be referred to as an ultrasound probe. The shaft 370 can be the same as shaft 270.

The shaft 370 has a body 300 formed of a monolithic thermoplastic material. The body 300 can be formed by injection molding, by extrusion, or by another process. The thermoplastic material consists of or comprises a biocompatible thermoplastic elastomer such as polyurethane, polycarbonate, polypropylene, polyethylene, pebax, polyether ether ketone, polyvinyl chloride, perfluoro alkoxy, polytetrafluoroethylene, silicone and/or another material. In other embodiments, the body 300 can be formed out of multiple materials or sections that can be bonded or attached to each other, such as through cross-linking, an adhesive, thermal bonding, and/or another technique. In some embodiments, the monolithic thermoplastic material can include internal reinforcements to improve the mechanical strength of the shaft 370.

A plurality of channels or lumens (in general, channels) are defined in the shaft 370 (e.g., in the body 300). The channels extend along at least a portion of the length of the shaft 370, which can be measured with respect to a first axis 311. The shaft 370 has a width or diameter that can be measured with respect to a second axis 312 that is orthogonal to the first axis 311. The shaft 370 can cylindrical or in another shape. The channels can extend from a proximal end 371 towards a distal end 372 of the shaft 370 (e.g., of the body 300).

The shaft 370 or body 300 includes an acoustic window 330 through which ultrasound energy can pass to a target volume in the patient. The thermoplastic material can have the same or a similar acoustic properties (e.g., acoustic impedance) to those of water to improve the acoustic transmission through the thermoplastic material and the acoustic window 330.

The body 300 includes or defines a tip 320. The tip 320 is integrally formed with and/or connected to the shaft 370 in a unitary (e.g., monolithic) structure that comprises the monolithic thermoplastic material. In another embodiment, the tip 320 can be over-molded onto the body 300. The tip 320 is angled relative to a central axis 374 of the shaft 370 (e.g., relative to the first axis 311) in a coudé style. A tip axis 322 that extends through the tip 320 and the central axis 374 can define a tip angle 324. The tip angle 324 can be in the range of about 120 degrees to about 150 degrees including any value or range between any two of the foregoing values. In other embodiments, the tip 320 can be straight (i.e., the tip angle 324 can be 180 degrees). Additionally or alternatively, the tip 320 can be tapered, have a ball end (olive tip), or have an elongated tapered curve (Tiemann Tip).

The tip 320 can define a hole or opening 326 (in general, opening) at a distal end of the tip 320. The opening 326 can be aligned with one or more of the channels in the shaft 370. For example, the opening 326 can be aligned with a guidewire channel in the shaft 370. A guidewire 430 can be inserted through the guidewire channel and the opening 326 to introduce an ultrasound therapy apparatus, including the shaft 370 and tip 320, into a patient.

The shaft 370 can include a plurality of markings or fiducial marks 380 that can represent respective insertion depths of the shaft 370. The markings 380 can be visible in MRI or other imaging. For example, the marking 380 can be radiopaque. The markings 380 can include marker bands that can be placed into and/or around the shaft 370. In some embodiments, the markings 380 can be formed by objects, such as beads, attached to the shaft 370. Additionally or alternatively, the markings 380 can include an object placed in the wall of the shaft 370, such as a metallic band placed or inserted into the wall of the shaft 370. For example, the shaft 370 can be cut parallel to plane 350 and a metallic band or ring can be attached between the two pieces of the shaft 370 formed by the cut. Additionally or alternatively, the markings 380 can include a material that is interwoven into the shaft (e.g., e.g., multiple materials pulled into a single extrusion).

Figure 4:
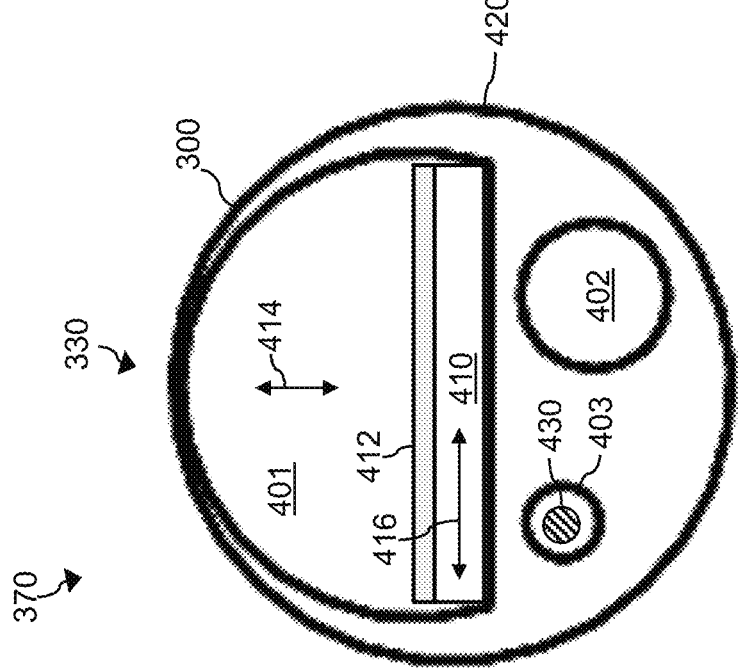
FIGS. 4-7 are cross sections of the shaft illustrated in FIG. 3 according to various embodiments.

FIG. 4 is a cross section of the shaft 370 through plane 350 in FIG. 3 according to an embodiment. In this embodiment, the body 300 defines three channels 401-403. The first channel 401 is configured to receive a printed circuit board (PCB) 410 on which ultrasound transducer elements 412 of the ultrasound array 255 are mounted. The first channel 401 can alternately be referred to as an ultrasound transducer channel 401.

The body 300 has an outer wall 420 that defines the outer diameter of the shaft 370 and that partially defines the ultrasound transducer channel 401. The outer wall 420 can have a local region of reduced thickness at the acoustic window 330 to allow for ultrasound energy produced by the ultrasound transducer elements 412 to pass through. The thickness of the outer wall 420 is smaller at the acoustic window 330 compared to other portions of the outer wall 420. The acoustic window 330 can be aligned with a first axis 414 that is orthogonal to a major plane of the PCB 410. The radius and diameter of the shaft 370 can be measured with respect to the first axis 414. The thickness of the outer wall 420 that passes through a second axis 416 that passes through the PCB 410 is greater than the thickness of the outer wall 420 at the acoustic window 330, where the second axis 416 is orthogonal to the first axis 414 and lies in the plane 350 (FIG. 3).

The second channel 402 is configured to receive a cooling fluid that can be circulated by a pump that is fluidly coupled to the second channel 402 and to a cooling fluid reservoir. The second channel 402 can alternately be referred to as a cooling fluid channel 402.

The ultrasound transducer channel 401 and the cooling fluid channel 402 can extend from the proximal end 371 of the shaft 370 (e.g., of the body 300) to a region between the proximal end 371 and the tip 320, such as a proximal end of the tip 320. The ultrasound transducer channel 401 and the cooling fluid channel 402 have closed distal ends and do not extend to the opening 326 on the tip 320.

The third channel 403 is configured to receive a guidewire 430 that can be used to introduce the ultrasound therapy apparatus, including the shaft 370 and tip 320, into a patient. The third channel 403 can extend from the proximal end 371 to the distal end 372 of the shaft 370 (e.g., of the body 300) and can be aligned with and connected to the opening 326 on the tip 320 such that the guidewire 430 can pass through the opening 326. The third channel 403 can alternately be referred to as a guidewire channel 403. A port plug can be disposed at the distal end of the guidewire channel 403 to prevent bodily fluids from entering.

Figure 5:
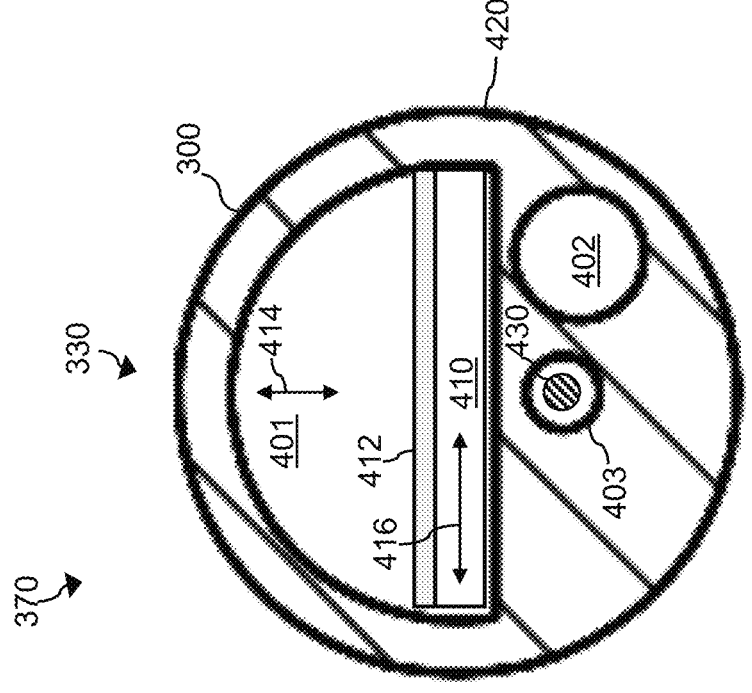

FIG. 5 is a cross section of the shaft 370 through plane 350 in FIG. 3 according to another embodiment. The cross section illustrated in FIG. 5 is the same as the cross section illustrated in FIG. 4 except that in FIG. 5, the outer wall 420 has a uniform or substantially uniform (e.g., within about 5%) thickness along the portion of the outer wall 420 that partially defines the ultrasound transducer channel 401. For example, in FIG. 5 the thickness of the outer wall 420 that passes through the second axis 416 can be the same or substantially the same as the thickness of the outer wall 420 at the acoustic window 330 (e.g., where the acoustic window 330 passes through the first axis 414).

The cooling fluid channel 402 and the guidewire channel 403 are illustrated in slightly different locations in FIG. 5 compared to FIG. 4 but can be in the same locations in FIG. 5 as in FIG. 4.

Figure 6A:
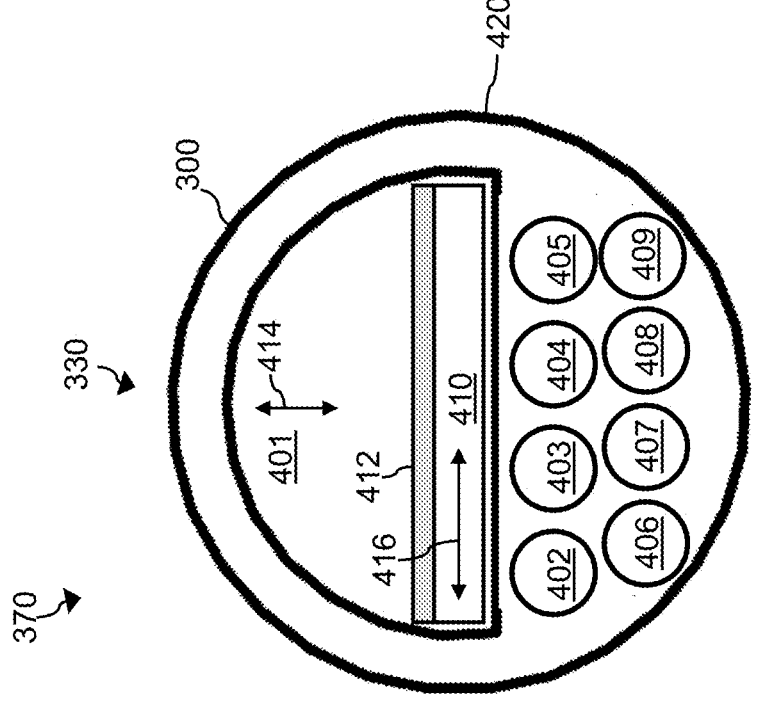

FIG. 6A is a cross section of the shaft 370 through plane 350 in FIG. 3 according to another embodiment. The cross section illustrated in FIG. 6 is the same as the cross section illustrated in FIG. 5 except that in FIG. 6A the body 300 defines nine channels 401-409. The body 300 can have additional or fewer channels in other embodiments.

A fourth channel 404 can be configured to receive bodily fluids, such as urine, for drainage from the patient. The bodily fluids can flow through the fourth channel 404 through gravity and/or by using a syringe. The fourth channel 404 can alternately be referred to as a bodily fluid channel 404. The bodily fluid channel 404 can extend from the proximal end 371 to the distal end 372 of the shaft 370 and can be aligned with and connected to the opening 326 on the tip 320 to receive the bodily fluids. Alternatively, the bodily fluid channel 404 can be aligned with another hole or opening on the tip 320 or shaft 370.

A fifth channel 405 can be configured to circulate ultrasound coupling fluid. The fifth channel 405 can alternately be referred to as an ultrasound coupling fluid channel 405. A distal end of the ultrasound coupling fluid channel 405 can be fluidly coupled to a distal end of the ultrasound transducer channel 401 such that the ultrasound coupling fluid travels in a first direction through the ultrasound transducer channel 401 and in a second (opposite) direction through the ultrasound coupling fluid channel 405. A proximal end of the fifth channel 405 and/or of the ultrasound transducer channel 401 can be fluidly coupled to a reservoir of ultrasound coupling fluid. Alternatively, the proximal ends of the ultrasound coupling fluid channel 405 and the ultrasound transducer channel 401 can be fluidly coupled to form a fluid loop that allows the ultrasound coupling fluid to be continually recirculated. A pump can be fluidly coupled to the ultrasound coupling fluid channel 405 and/or to the ultrasound transducer channel 401 to circulate the ultrasound coupling fluid. Alternatively, a syringe can be used to introduce and/or circulate the ultrasound coupling fluid.

A sixth channel 406 can be configured to receive a tool such as a medical instrument. The sixth channel 406 can alternately be referred to as a tool channel 406. The tool channel 406 can extend from the proximal end 371 to the distal end 372 of the shaft 370 (e.g., of the body 300) and can be aligned with and connected to the opening 326 on the tip 320 to allow the tool pass through to the patient. Alternatively, the tool channel 406 can be aligned with another hole or opening on the tip 320 or shaft 370.

Seventh and eighth channels 407, 408 can be configured to receive electrical connectors, wires, and/or sensors. Channels 407, 408 can alternately be referred to as an electrical connector channels. The electrical connectors and/or wires can be electrically coupled to the PCB 410 and/or to a tool in tool channel 406 through connections between (a) channel 407 or 408 and (b) channel(s) 401 and/or 406. Channels 407, 408 may house sensors for temperature, pressure, or other measurements, and may be terminated at various lengths throughout the shaft 300, according to where the sensor measurement is required within the patient.

A nineth channel 409 can be configured to receive and deliver one or more drugs, medications, and/or other substances to a target location such as during a medical procedure.

Figure 6B:
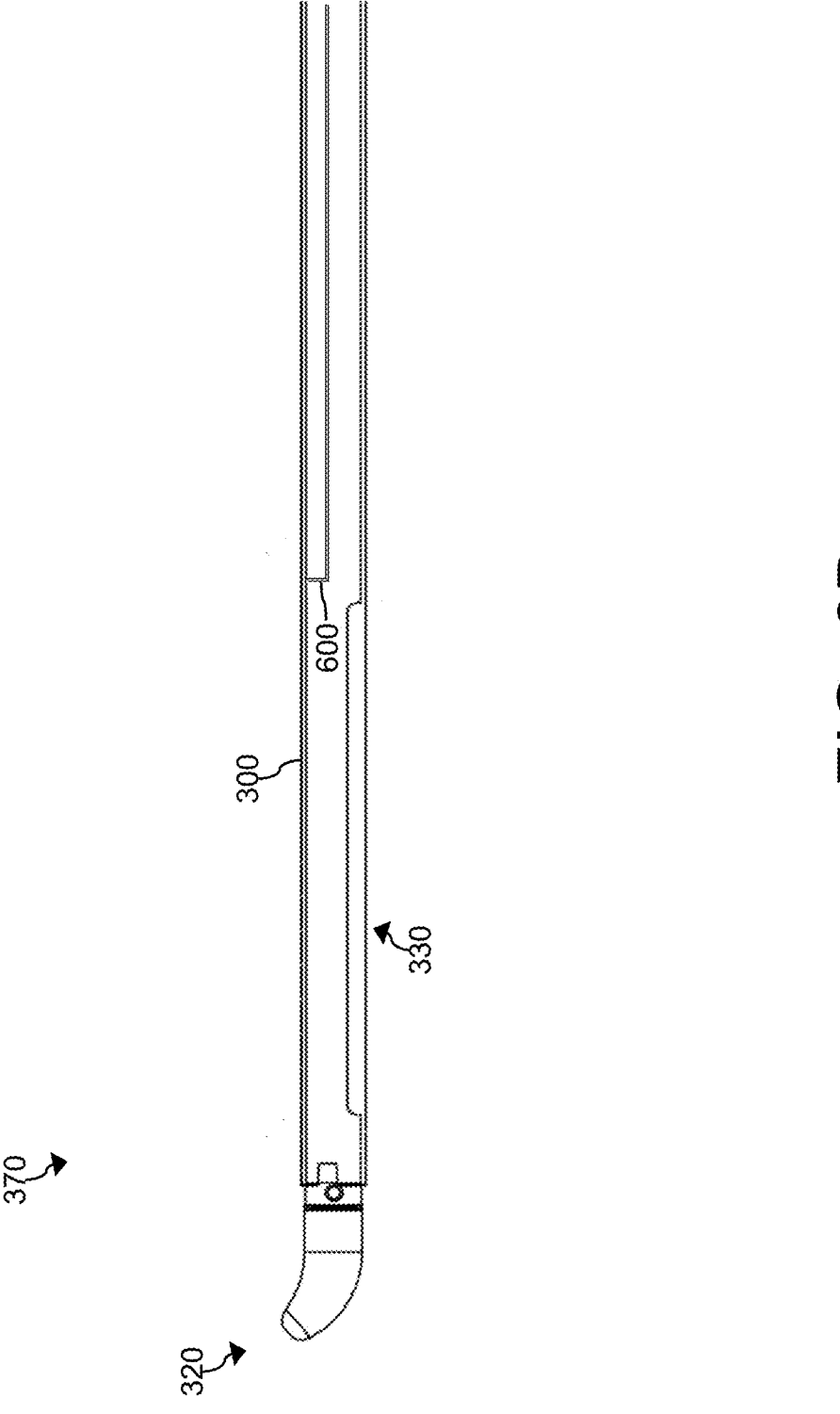

The electrical conductors or wires may be inserted through the channels and connected to the sensors, or in alternative embodiments, the electrical conductors 600 are extruded into the shaft and are part of the main body 300, as shown for example in FIG. 6B.

The channels 402-408 are illustrated as having the same diameter in FIG. 6A. In other embodiments, at least one of the channels 402-408 can have a larger diameter than the other channels 402-408 Some or all of the channels 402-408 can have different diameters than the other channels 402-408. The channels 402-408 can have different relative arrangements than that illustrated in FIG. 6A. For example, channel 407 can be located next to channel 405 instead of next to channel 406.

One or more other channels can be included in the body 300, in addition to or instead of one or more of the channels 402-408. For example, one or more channels can be fluidly coupled to one or more respective balloons attached to the body 300 to inflate/deflate the respective balloon(s). Another channel can be used to inject or introduce a substance into the subject. For example, a numbing agent or a lubricating gel can be injected/introduced into the urethra and/or the bladder.

The outer wall 420 can have a local region of reduced thickness at the acoustic window 330, as illustrated in FIG. 4.

Figure 7:
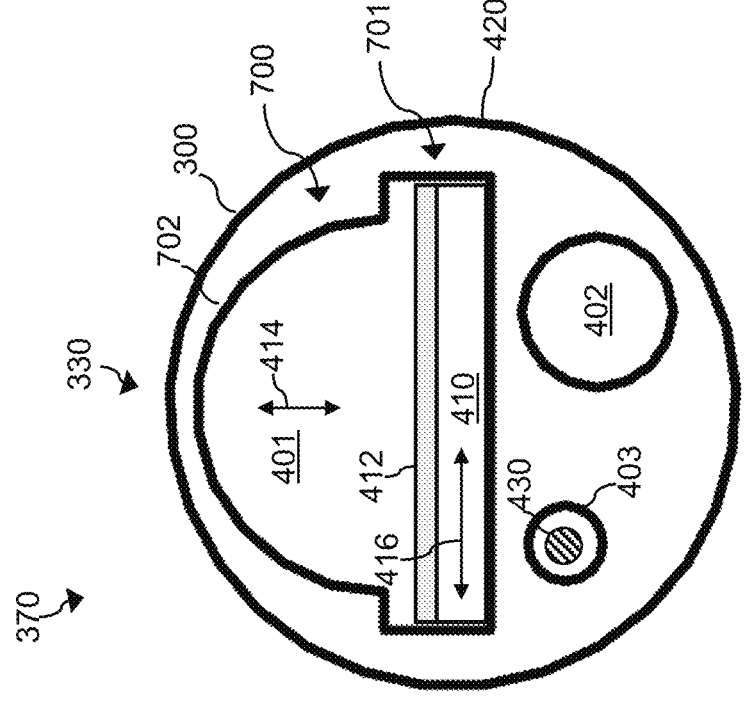

FIG. 7 is a cross section of the shaft 370 through plane 350 in FIG. 3 according to another embodiment. The cross section illustrated in FIG. 7 is the same as the cross section illustrated in FIG. 5 except that in FIG. 7 the ultrasound transducer channel 401 has a hat shape 700. The hat shape 700 includes a rectangular portion 701 configured to secure the PCB 410 including the ultrasound elements 412 and a rounded portion 702 through which the ultrasound coupling fluid flows.

The embodiments illustrated in FIGS. 4-7 can be combined in any manner. For example, the embodiment illustrated in FIG. 7 can include additional channels 402-408 and/or an outer wall 420 having a uniform or substantially uniform thickness along the portion of the outer wall 420 that partially defines the ultrasound transducer channel 401. Similarly, any of the cross sections illustrated in FIGS. 4-6 can include an ultrasound transducer channel 401 having a hat shape 700.

Figure 8:
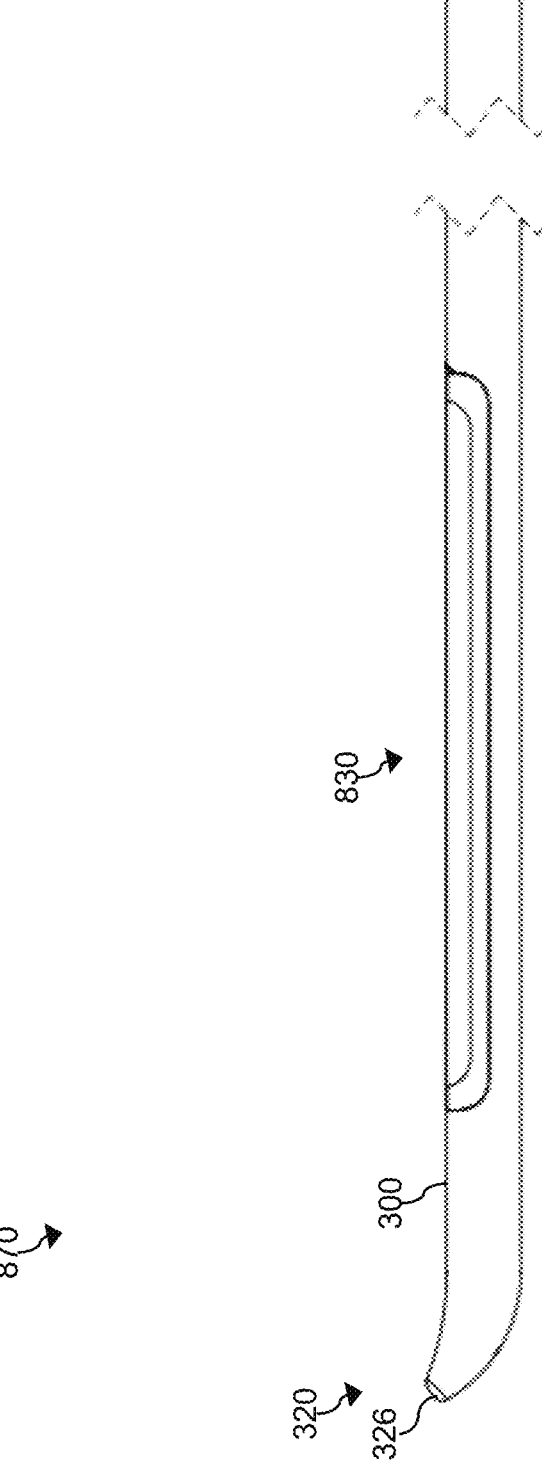
FIG. 8 is a side view of a shaft for an ultrasound therapy apparatus according to another embodiment.

FIG. 8 is a side view of a shaft 870 for an ultrasound therapy apparatus according to another embodiment. The shaft 870 is the same as the shaft 370 except that the shaft 870 includes an acoustic window 830 that is attached, welded, and/or adhered to the body 300.

Figure 9:
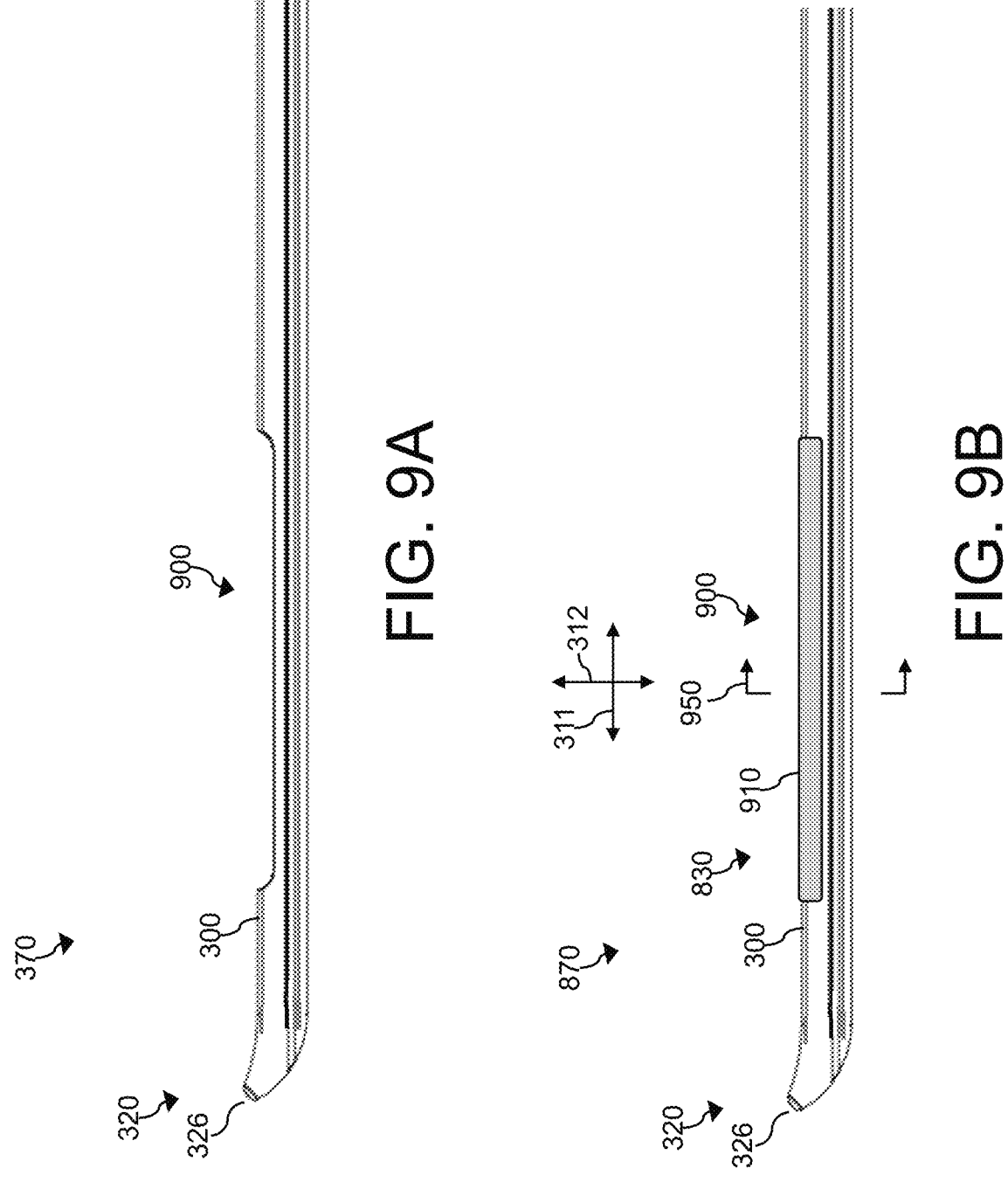
FIG. 9A illustrates a first step for manufacturing the shaft illustrated in FIG. 8.
FIG. 9B illustrates a second step for manufacturing the shaft illustrated in FIG. 8.

The shaft 870 can be manufactured by creating the shaft 370 illustrated in FIG. 3 and then forming a hole 900 in the body 300 that corresponds to the location of the acoustic window 830, as illustrated in FIG. 9A. The hole 900 has a length and width that corresponds to the ultrasound array 255 of ultrasound transducer elements 412 in the ultrasound transducer channel 401, such that ultrasound energy produced by the ultrasound transducer elements 412 passes through the hole.

Material can be removed from the shaft 370 to form the hole 900 through cutting, machining, or another process. A section of material 910 that conforms to the shape of the hole 900 is then placed on the hole 900 and attached, welded (e.g., using a thermoplastic weld), and/or adhered to the body 300 to form the shaft 870, as illustrated in FIG. 9B. The material 910 can consist of or comprise the same material as the thermoplastic material used to form the body 300. Alternatively, the material 910 can consist of or comprise a different thermoplastic material as the thermoplastic material used to form the body 300. The material 910 can consist of or comprise another material in other embodiments. The attachment, welding, and/or adhesion of the material 910 to the body 300 forms a fluid seal between the material 910 and the body 300.

The material 910 has a length and a width, as measured with respect to the first and second axes 311, 312, respectively, that are larger than the hole 900 so that the material 910 can be attached to the body 300 to cover the hole 900.

An advantage of the shaft 870 is that the acoustic window 830 can be formed out of a customized material (material 910) that can more closely match the acoustic properties of water to allow for improved acoustic transmission while another material, that may have superior structural properties, can be used to form the body 300. Additionally or alternatively, the acoustic window 830 can be formed out of a thinner material (for improved acoustic transmission) than would be practical to form using the manufacturing methods (e.g., injection molding) used to form the body 300.

Figure 10:
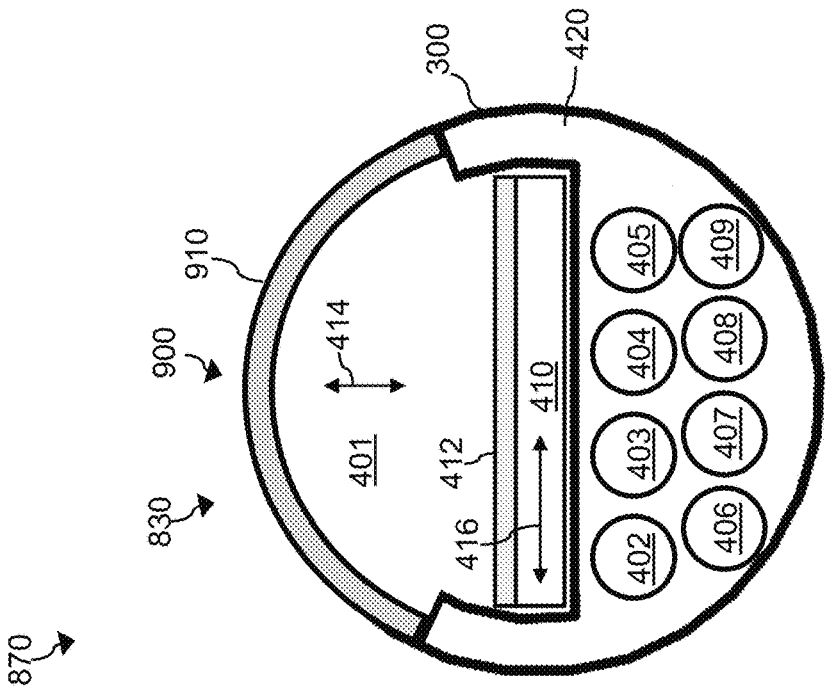
FIG. 10 is an example cross section of the shaft illustrated in FIG. 8.

A cross section through plane 950 (FIG. 9B) of the shaft 870 can be the same as any of the cross sections illustrated in FIGS. 4-7 except that the acoustic window 330 is formed out of the material 910 instead of monolithically formed with the body 300 (e.g., by the outer wall 420). FIG. 10 is an example cross section through plane 950 of the shaft 870 in an embodiment corresponding to the cross section illustrated in FIG. 6A.

Figure 11:
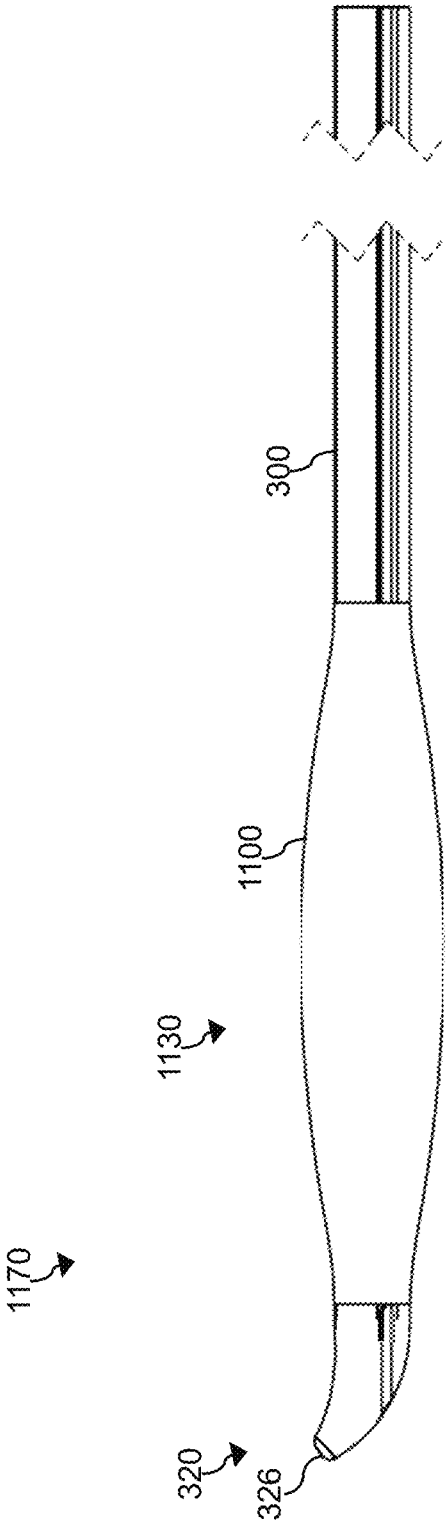
FIG. 11 is a side view of a shaft for an ultrasound therapy apparatus according to another embodiment.

FIG. 11 is a side view of a shaft 1170 for an ultrasound therapy apparatus according to another embodiment. The shaft 1170 is the same as the shaft 370 except that the shaft 1170 includes an acoustic window 1130 that comprises a balloon 1100.

Figures 12A, 12B:
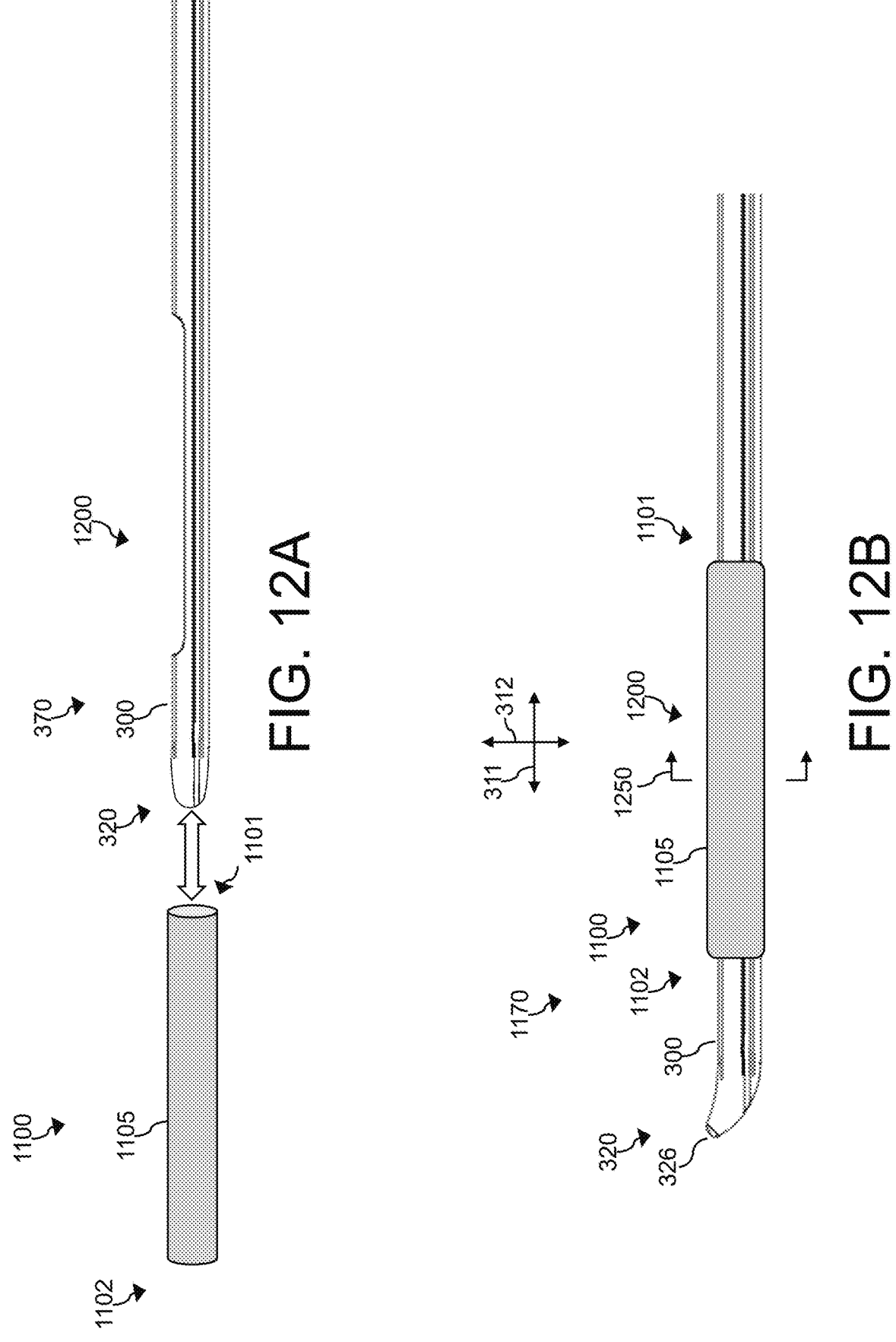
FIG. 12A illustrates a first step for manufacturing the shaft illustrated in FIG. 11.
FIG. 12B illustrates a second step for manufacturing the shaft illustrated in FIG. 11.

The shaft 1170 can be manufactured by creating the shaft 370 illustrated in FIG. 3 and then forming a hole 1200 in the body 300 that corresponds to the location of the acoustic window 1130, as illustrated in FIG. 12A. The hole 1200 can be formed before the tip 320 is optionally bent. A balloon 1100 having a shape that conforms to the shape of the hole 1200 is then placed over the body 300, such as over the tip 320, to cover the hole 1200. The balloon 1100 is generally in the form of a cylinder with open ends 1101, 1102 and a wall 1105 that extends between the open ends 1101, 1102. The tip 320 can be inserted through the first open end 1101 and then through the second open end 1102.

The balloon 1100 is placed so that the wall 1105 covers the hole 1200, as illustrated in FIG. 12B. After the balloon 1100 is placed over the hole 1200, the open ends 1101, 1102 are attached to the body 300 to form the shaft 1170. The open ends 1101, 1102 can be attached and fluidly sealed to the body 300 using an adhesive, laser welds, and/or another attachment method. The balloon 1100 can consist of or comprise of thin-walled, biocompatible thermoplastics such as polyurethane, polycarbonate, polypropylene, polyethylene, pebax, polyether ether ketone, polyvinyl chloride, perfluoro alkoxy, polytetrafluoroethylene, nylon, silicone and/or another material. The balloon 1100 may or may not including a coating to allow drug delivery, to affect lubricity, and/or to create fiduciaries.

The balloon 1100 is configured to retain the ultrasound coupling fluid in the ultrasound transducer channel 401. The balloon 1100 can transition between an inflated state and a deflated state in response to an increase or decrease of pressure, respectively, applied by the ultrasound coupling fluid in the ultrasound transducer channel 401. The balloon 1100 can be configured to symmetrically expand (or substantially symmetrically expand (e.g., having a variation of radius within about 5%)) in the inflated state, as illustrated in FIG. 11. The balloon 1100 is in the deflated state in FIG. 12B.

The balloon 1100 has a length, as measured with respect to the first axis 311, that is larger than the hole 900 such that the first and second ends 1101, 1102 can be attached to the body 300.

A symmetrical balloon can be used to open an anatomical orifice or vessel, such as the urethra or bladder in the patient and/or to secure the shaft 1170 and the ultrasound therapy apparatus within the anatomical orifice or vessel in the patient during ultrasound therapy.

Figures 13A, 13B:
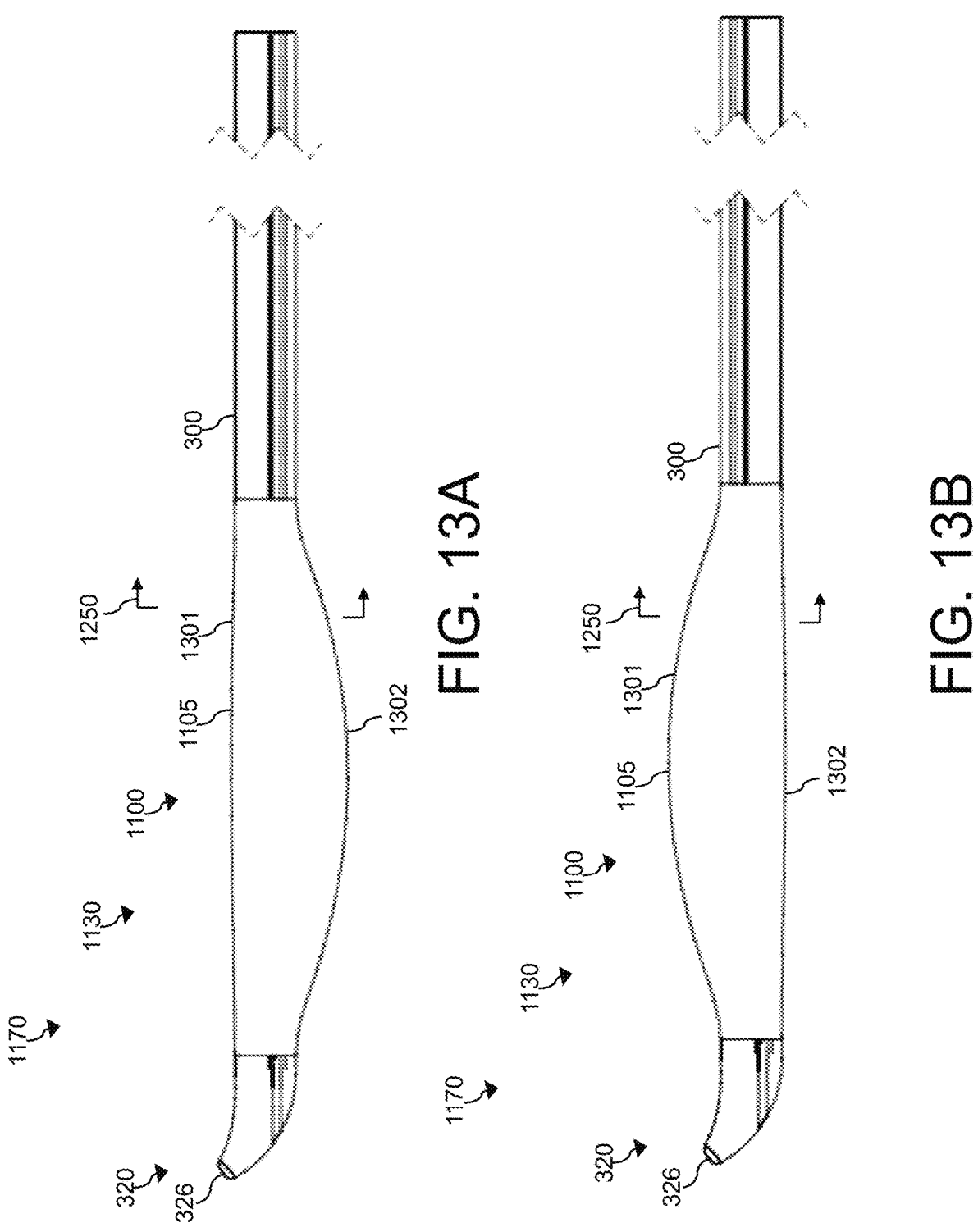
FIGS. 13A and 13B illustrate alternative embodiments of the shaft illustrated in FIG. 11.

Alternatively, the balloon 1100 can be configured to asymmetrically expand in the inflated state, as illustrated in FIG. 13A. The thickness of the wall 1105 can be larger on a first side 1301 of the balloon 1100 compared to a second side 1302 of the balloon 1100 such that the balloon 1100 expands preferentially towards the second side 1302. The first side 1301 can define the acoustic window 1130. In another embodiment, the thickness of the wall 1105 can be larger on the second side 1302 of the balloon 1100 compared to the first side 1301 of the balloon 1100 such that the balloon 1100 expands preferentially towards the first side 1301, which defines the acoustic window 1130, as illustrated in FIG. 13B.

An asymmetric offset balloon can be used to push the acoustic window 1130 towards or away from an anatomical region, for example to provide increased control over the depth and/or direction of the ultrasound energy.

Alternative balloon shapes, such as tapered, conical, or square, which can be symmetric or asymmetric, can be used in some embodiments.

A cross section of the shaft 1170 through plane 1250, for the embodiments illustrated in FIGS. 12B, 13A, and 13B, can be the same as any of the cross sections illustrated in FIGS. 4-7 except that the acoustic window 300 is formed out of a balloon 1100 instead of monolithically formed with the body 300 (e.g., by the outer wall 420). The balloon 1100 extends along the perimeter or circumference of the body 300.

Figure 14:
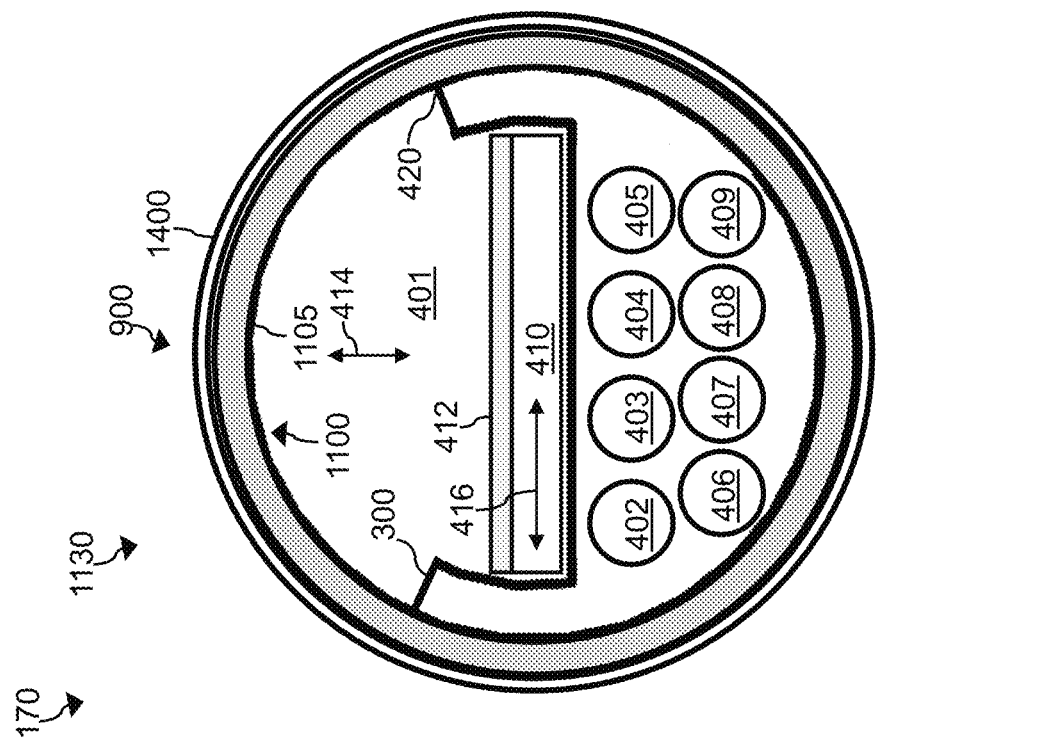
FIG. 14 is an example cross section of the shaft illustrated in FIG. 12B.

FIG. 14 is an example cross section through plane 1250 of the shaft 1170 for the embodiment illustrated in FIG. 12B. The thickness of the wall 1105 of the balloon 1100 can be measured with respect to axis 414. The cross section illustrated in FIG. 14 corresponds to the cross section illustrated in FIG. 6A. In other embodiments, the cross section can include any number and/or configuration of channels 401-409 according to the embodiments illustrated in FIGS. 4-7. An optional coating 1400 is disposed on the balloon 1100. The optional coating 1400 can include drug(s) and/or lubricant(s) to be introduced and/or used during an ultrasound procedure such as an ultrasound ablation procedure. Additionally or alternatively, the coating 1400 can include or form fiducials that can be used to guide the ultrasound therapy apparatus.

Figure 15B:
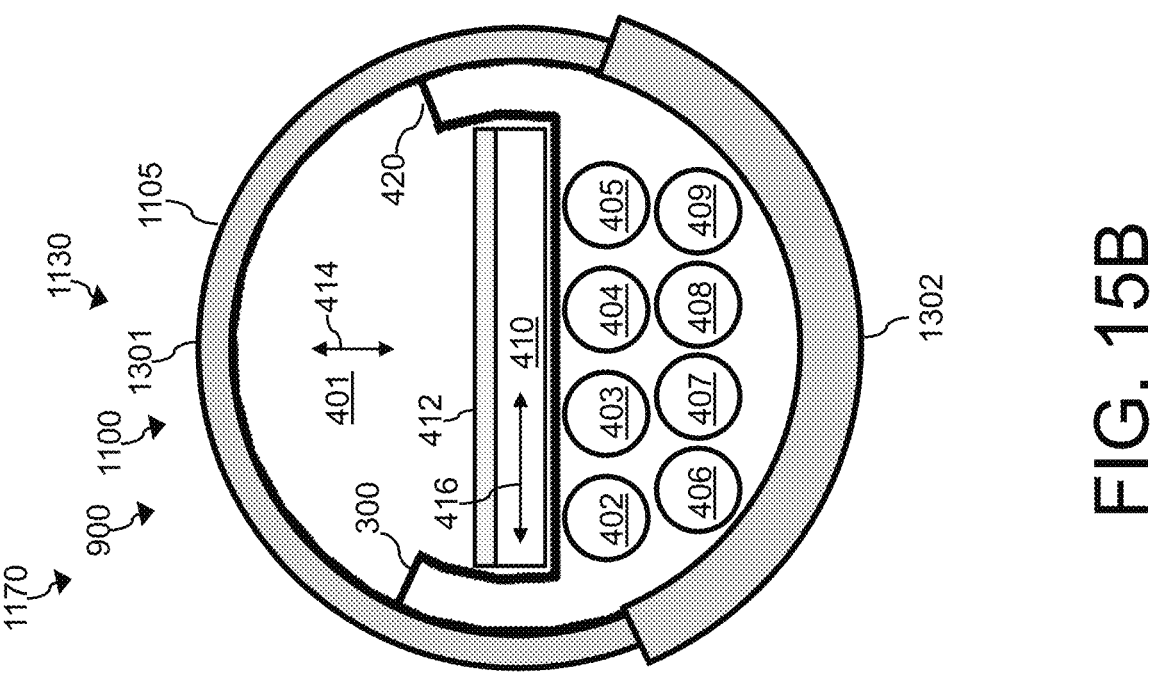
FIGS. 15A and 15B are example cross sections of the shafts illustrated in FIGS. 13A and 13B, respectively, when the asymmetrical balloons are in the deflated state.
Figure 15A:
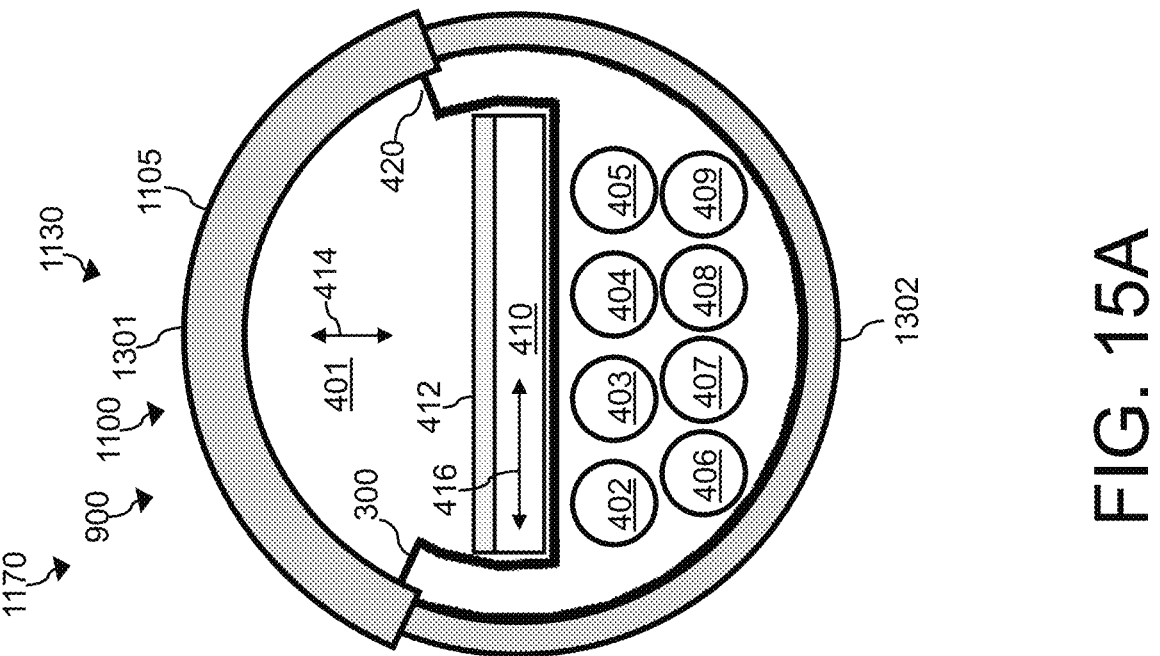

FIGS. 15A and 15B are example cross sections through plane 1250 of the shaft 1170 for the embodiments illustrated in FIGS. 13A and 13B, respectively, when the asymmetrical balloons 1100 are in the deflated state. In FIG. 15A, the thickness of the wall 1105 of the balloon 1100, as measured with respect to axis 414, is larger on the first side 1301 compared to the second side 1302, which causes the balloon 1100 to expand preferentially towards the second side 1302. In FIG. 15B, the thickness of the wall 1105 of the balloon 1100, as measured with respect to axis 414, is larger on the second side 1302 compared to the first side 1301, which causes the balloon 1100 to expand preferentially towards the first side 1301. The cross sections illustrated in FIGS. 15A and 15B correspond to the cross section illustrated in FIG. 6A. In other embodiments, the cross sections can include any number and/or configuration of channels 401-409 according to the embodiments illustrated in FIGS. 4-7.

Figure 16:
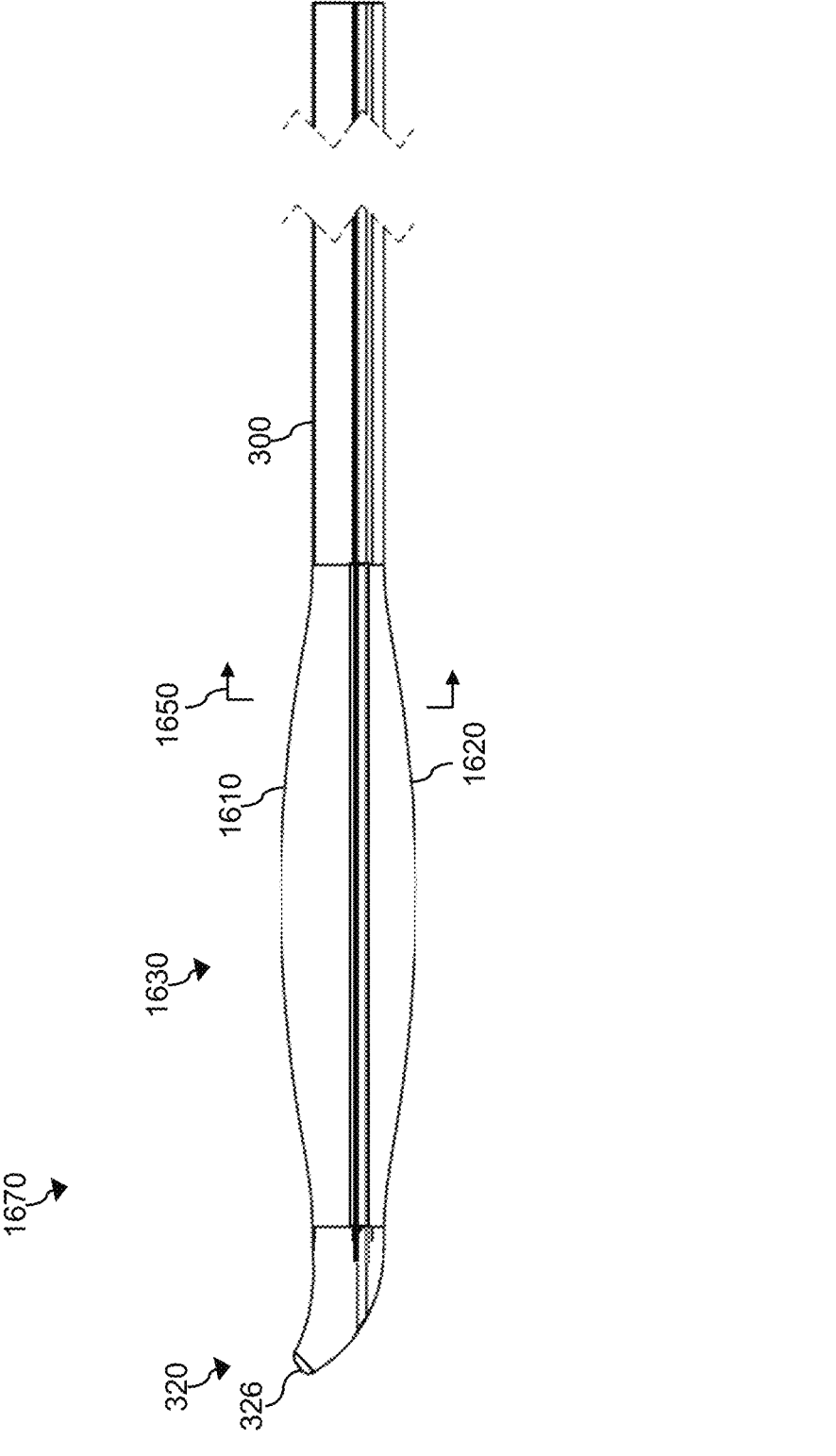
FIG. 16 is a side view of a shaft for an ultrasound therapy apparatus according to another embodiment.

FIG. 16 is a side view of a shaft 1670 for an ultrasound therapy apparatus according to another embodiment. The shaft 1670 is the same as the shaft 1170 except that the shaft 1670 includes two balloons 1610, 1620. The first acoustic balloon 1610 defines an acoustic window 1630. The first and second balloons 1610, 1620 can be inflated and deflated independently of each other.

Figure 17:
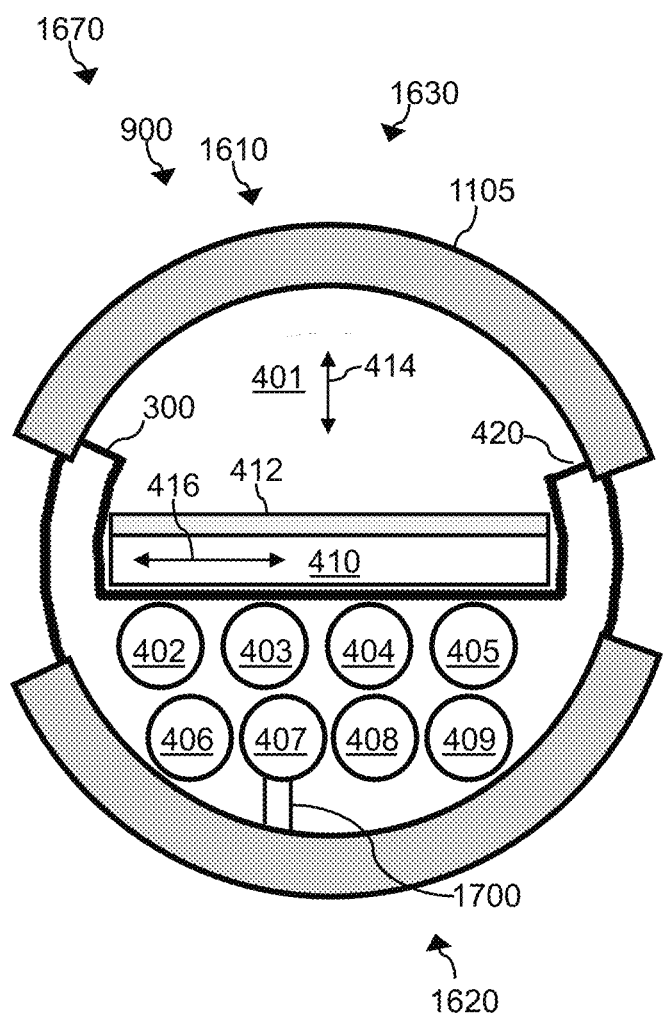
FIG. 17 is an example cross section of the shaft illustrated in FIG. 16 when the first and second balloons are in the deflated state.

FIG. 17 is an example cross section through plane 1650 of the shaft 1670 illustrated in FIG. 16 when the first and second balloons 1610, 1620 are in the deflated state. The first balloon 1610 is in fluid communication with the ultrasound coupling fluid in the ultrasound transducer channel 401. The first balloon 1610 can be inflated and deflated in response to an increase or decrease of pressure, respectively, applied by the ultrasound coupling fluid in the ultrasound transducer channel 401, in the same manner as the balloon 1100.

The second balloon 1620 is in fluid communication with the seventh channel 407 (or another channel other than the ultrasound transducer channel 401) to receive a fluid such as through a conduit 1700. The second balloon 1610 can be inflated and deflated in response to an increase or decrease of pressure, respectively, applied by the fluid from the channel 407 (or another channel other than the ultrasound transducer channel 401).

The first and second balloons 1610 and 1620 have respective thicknesses that can be measured with respect to the axis 414. The thickness and/or material of the first balloon 1610 can be the same or different than the thickness and/or the material, respectively, of the second balloon 1620.

The cross section illustrated in FIG. 17 corresponds to the cross section illustrated in FIG. 6A. In other embodiments, the cross section can include any number and/or configuration of channels 401-407 according to the embodiments illustrated in FIGS. 4-7.

An advantage of having two balloons on shaft 1670 is that each balloon can be inflated and deflated independently to provide more precise control of their size and inflation state, for example to conform to each patient's anatomy.

Figure 18:
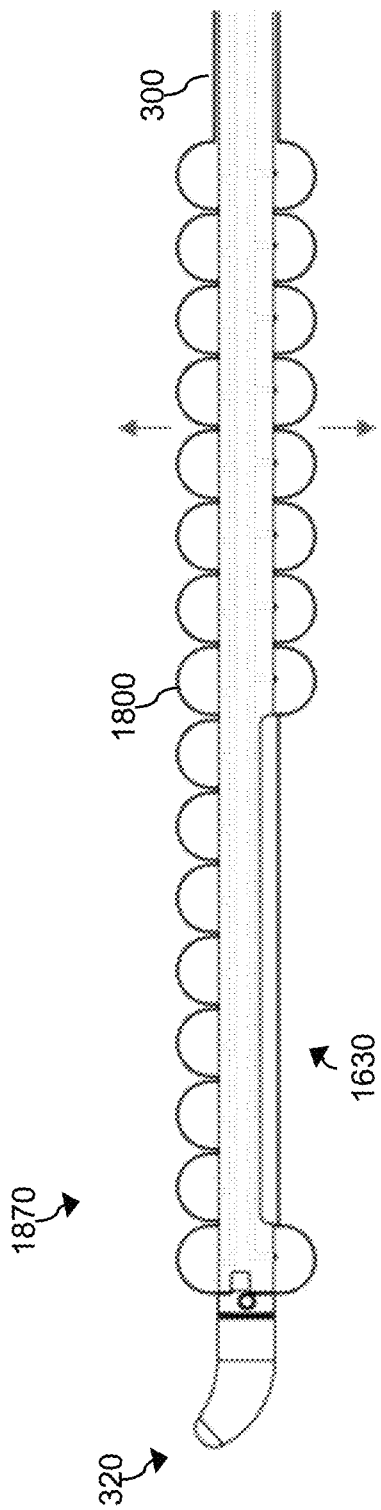
FIG. 18 is a side view of a shaft for an ultrasound therapy apparatus according to another embodiment.

In other embodiments, a shaft 1870 includes a plurality of balloons 1800, as shown in FIG. 18. The inflation state of the balloons 1800 can be controlled individually, in pairs, in groups, or together. Shaft 1870 is otherwise the same as shaft 1670.

Figure 19A:
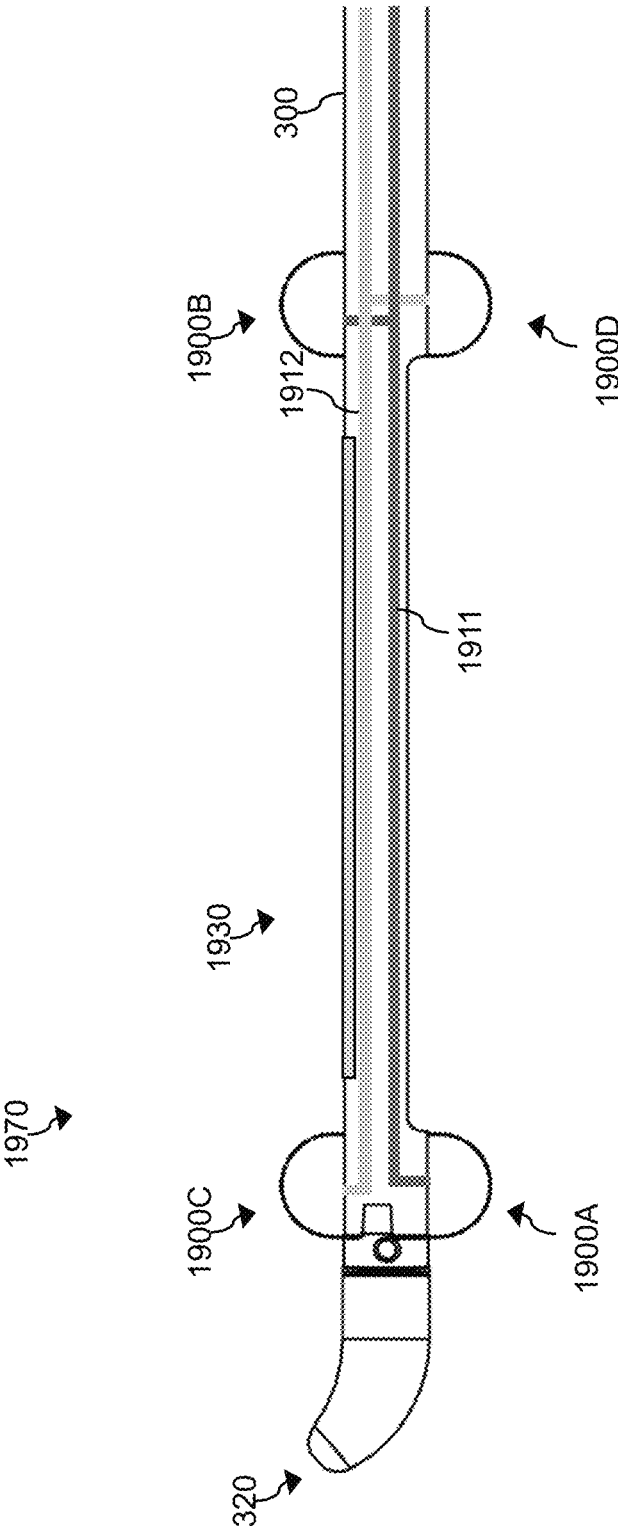
FIG. 19A is a side view of a shaft for an ultrasound therapy apparatus according to another embodiment.

In another embodiment, a shaft 1970 can include two pairs of balloons 1900A, B and 1900C, D, as illustrated in FIG. 19A. Each pair of balloons can be inflated independently through respective inflation channels 1911, 1912. Inflation channel 1911 is fluidly coupled to a first pair of balloons 1900A, 1900B. Inflation channel 1912 is fluidly coupled to a second pair of balloons 1900C, 1900D.

Figures 19B, 19C:
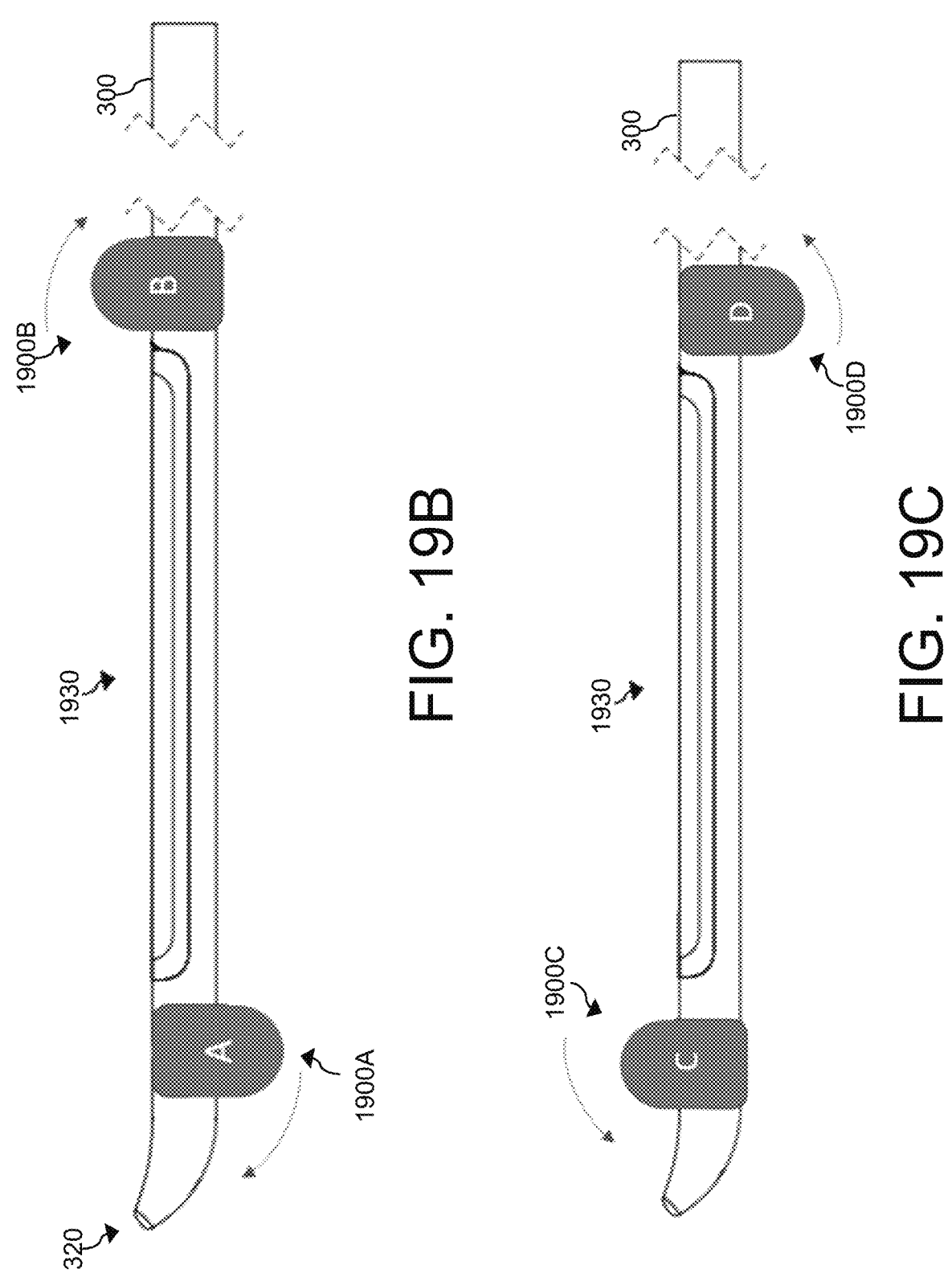
FIG. 19B is a side view of the shaft illustrated in FIG. 19A in a first state.
FIG. 19C is a side view of the shaft illustrated in FIG. 19A in a second state.

The pairs of balloons 1900A-D can be selectively inflated to adjust an angle or tilt of the tip 320 and an acoustic window 1930, for example as illustrated schematically in FIGS. 19B and 19C. In FIG. 19B, only the first pair of balloons 1900A, 1900B is inflated to drive the tip 320 and a distal end of the acoustic window 1930 upwards. In FIG. 19C, only the second pair of balloons 1900C, 1900D is inflated to drive the tip 320 and a proximal end of the acoustic window 1930 downwards. The angle or tilt of the tip 320 and the acoustic window 1930 can be adjusted during introduction of the ultrasound therapy apparatus (e.g., to enhance navigation) and/or at a target location of the ultrasound therapy apparatus (e.g., to align the acoustic window 1930 with a target treatment volume).

Figure 20:
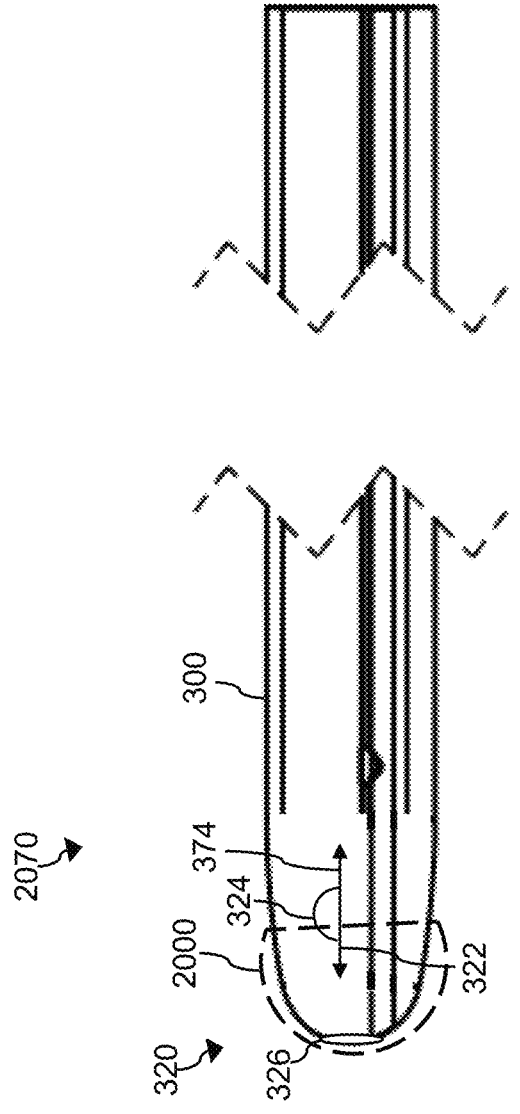
FIG. 20 is a side view of a shaft for an ultrasound therapy apparatus according to another embodiment.

FIG. 20 is a side view of a shaft 2070 for an ultrasound therapy apparatus according to another embodiment. The shaft 2070 can be the same as any of the shafts 370, 870, 1170, 1670, 1870, and/or 1970 except that in shaft 2070 the tip 320 is straight instead of angled. For example, the tip axis 322 can be aligned (e.g., collinear) with the central axis 374 such that the tip angle 324 is about 180 degrees. In other embodiments, the opening 326 can be offset with respect to the central axis 374.

When a shaft includes a bent tip, the shaft is initially formed as the shaft 2070 with a straight tip 320. To form a bent tip, the straight tip 320 is heated and a force is applied to the hot tip in the direction of the bend to form a desired tip angle 324. Additionally or alternatively, the straight tip 320 can be heated and placed in a mold to form a bent tip. The bent tip can remain in the mold as it cools. The bent tip remains in the bent position after it cools.

In some embodiments, a material 2000 can be overmolded onto the tip 320. The overmolded material 2000 can be different than the thermoplastic material that forms the monolithic body 300 of the shaft 1670. The overmolded material 2000 can have a lower coefficient of friction compared to the external surface of the tip 320 (e.g., of the thermoplastic material that forms the monolithic body 300) to allow the tip 320 to be inserted to the patient's orifice (e.g., urethra or bladder) with a lower force compared to when then tip 320 does not include the overmolded material 2000.

Figure 21:
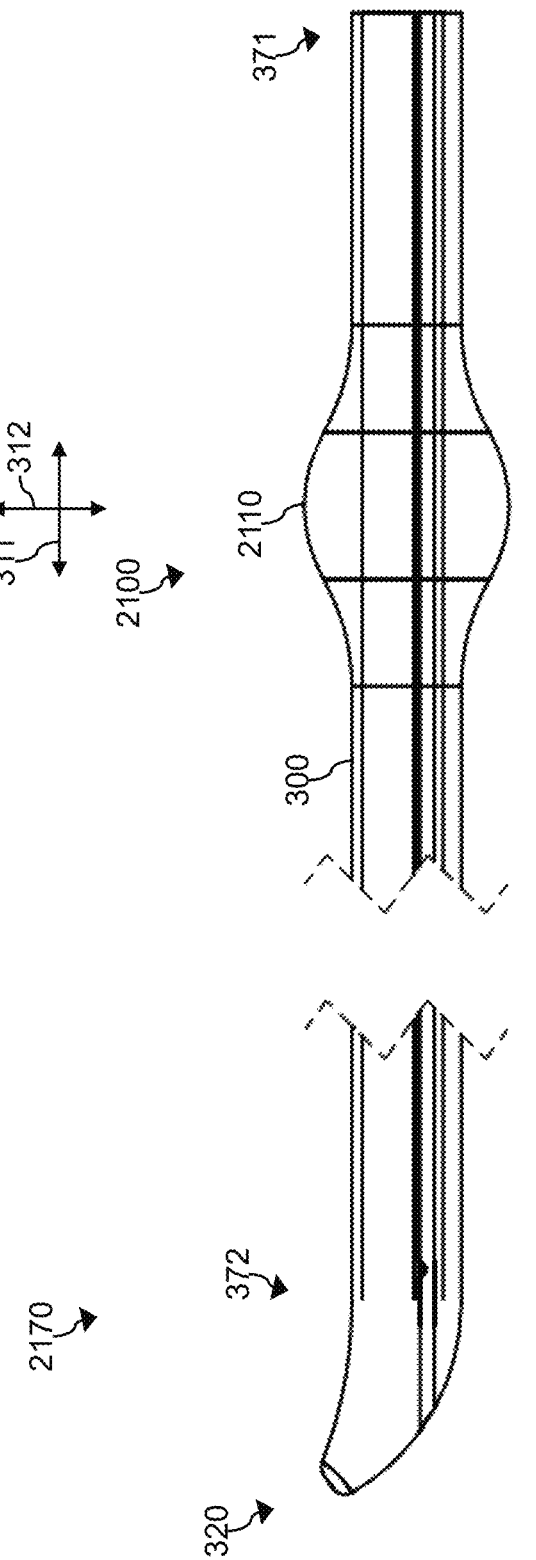
FIG. 21 is a side view of a shaft for an ultrasound therapy apparatus according to another embodiment.

FIG. 21 is a side view of a shaft 2170 for an ultrasound therapy apparatus according to another embodiment. The shaft 2170 can be the same as any of the shafts 370, 870, 1170, 1670, 1870, 1970, and/or 2070 except that in shaft 2170, a proximal portion 2100 of the body 300 includes a bulge or bump 2110 (in general, bulge 2110). The width or diameter of the body 300 is larger at the bulge 2110 compared to the rest of the body 300. The proximal portion 2100 is located closer to the proximal end 371 than to the distal end 372 of the shaft 2170 (e.g., of the body 300). The bulge 2110 can be symmetric with respect to the central axis of the shaft 2170, which is parallel to the first axis 311.

The bulge 2110 can be formed during manufacturing of the shaft 2170. For example, when the shaft 2170 is formed in an extrusion process, the bulge 2110 can be formed controlling and adjusting the speed of the extrusion, where the extrusion speed is slower when forming the bulge 2110 compared to when forming the rest of the shaft 2170. When the shaft 2170 is formed in an injection mold process, the design of the mold can be configured to form the bulge 2110.

The bulge 2110 can deflect bodily fluids that may flow out of the subject along or around the shaft 2170. For example, when the shaft 2170 is interested into a male urethra, urine may flow along or around the shaft 2170. This is undesirable as the urine can contact a robotic positioning system for the ultrasound therapy apparatus and may cause damage to the robotic positioning system, such as corrosion of gears in the robotic positioning system. The bulge 2110 can promote or cause the bodily fluids, such as urine, to drip off of the shaft 2170 before reaching sensitive equipment such as the robotic positioning system.

The tip 320 is illustrated as angled in FIG. 21 but the tip 320 can be straight in another embodiment.

In some embodiments, one or more of the shafts described herein (e.g., shaft 370, 870, 1170, 1670, 1870, 1970, 2070, and/or 2170) can include internal reinforcements to improve the mechanical strength of the shaft(s). The internal reinforcements can include over molded stiffeners and/or braiding. An example of a stiffener is alloy that can be available in different thicknesses and different stiffnesses. An example of braiding is forming or winding a braiding wire or thermoplastic into or onto the shaft. The braiding wire or thermoplastic (e.g. liquid crystal polymer) can be interwoven into the shaft material as it is formed (e.g., extruded).

The internal reinforcements can increase the rigidity of the shaft. A rigid shaft can be useful to translate force during a medical procedure, for example to shift anatomy and position the ultrasound therapy apparatus closer to a target treatment volume.

The invention should not be considered limited to the particular embodiments described above, but rather should be understood to cover all aspects of the invention as fairly set out in the attached claims. Various modifications, equivalent processes, as well as numerous structures to which the invention may be applicable, will be apparent to those skilled in the art to which the invention is directed upon review of this disclosure. The claims are intended to cover such modifications and equivalents.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. An ultrasound probe comprising:
a shaft including a monolithic thermoplastic body having an outer wall that defines a diameter of the shaft, the monolithic thermoplastic body defining a plurality of channels that extend from a proximal end of the shaft, the plurality of channels including:
an ultrasound transducer channel, and
a cooling channel;
a tip disposed at a distal end of the shaft; and
a printed circuit board (PCB) including at least one ultrasound transducer element electrically connected to the printed circuit board, the PCB disposed in the ultrasound transducer channel, wherein the outer wall defines an acoustic window that is aligned with the at least one ultrasound transducer element.

2. The ultrasound probe of claim 1, wherein the outer wall has a tapered thickness at the acoustic window.

3. The ultrasound probe of claim 2, wherein:
the acoustic window is aligned with a first axis that is orthogonal to a major plane of the printed circuit board,
a thickness of the outer wall at a location that passes through the first axis is smaller than a thickness of the outer wall at a location that passes through a second axis that passes through the PCB and that is orthogonal to the major plane,
a width of the PCB is measured with respect to the second axis, and
a length of the PCB is measured with respect to a third axis that is orthogonal to the first and second axes.

4. The ultrasound probe of claim 1, wherein the ultrasound transducer channel includes a rectangular portion configured to secure the PCB and a rounded portion to receive an ultrasound coupling fluid.

5. The ultrasound probe of claim 1, wherein the tip has a tip angle defined by a tip axis that passes through an opening of the tip and a central axis of the shaft, the central axis orthogonal to the diameter of the shaft and parallel to a length of the shaft, the tip angle greater than equal to 120 degrees and less than or equal to 150 degrees.

6. The ultrasound probe of claim 1, wherein the plurality of channels includes a guidewire channel that extends from the proximal end of the shaft to the tip, the guidewire channel connected to an opening defined at distal end of the tip, the guidewire channel and the opening configured to receive a guidewire.

7. The ultrasound probe of claim 1, wherein the plurality of channels includes a bodily fluids channel that extends from the proximal end of the shaft to the tip, the bodily fluids channel connected to an opening defined at a distal end of the tip, the bodily fluids channel and the opening configured to receive bodily fluids from the patient.

8. The ultrasound probe of claim 1, wherein the plurality of channels includes an ultrasound coupling fluid channel having a distal end that is fluidly coupled to the ultrasound transducer channel to allow an ultrasound coupling fluid to circulate between the ultrasound coupling fluid channel and the ultrasound transducer channel.

9. The ultrasound probe of claim 1, wherein the monolithic thermoplastic body includes the tip.

10. The ultrasound probe of claim 1, wherein the plurality of channels includes a tool channel configured to receive a medical instrument.

11. The ultrasound probe of claim 1, wherein the plurality of channels includes a drug delivery channel configured to introduce a drug to a target location.

12. An ultrasound probe comprising:

a shaft including a monolithic thermoplastic body having an outer wall that defines a diameter of the shaft, the monolithic thermoplastic body defining a plurality of channels that extend from a proximal end of the shaft, the plurality of channels including:

an ultrasound transducer channel, and a cooling channel;

a tip disposed at a distal end of the shaft;

a printed circuit board (PCB) including at least one ultrasound transducer element electrically connected to the printed circuit board, the PCB disposed in the ultrasound transducer channel, wherein the outer wall defines a hole that is aligned with and that extends along the at least one ultrasound transducer element; and a section of material covering the hole to form an acoustic window, the section of material attached to the monolithic thermoplastic body to form a fluid seal between the section of material and the monolithic thermoplastic body.

13. The ultrasound probe of claim 12, wherein the monolithic thermoplastic body and the section of material are formed of the same material.

14. The ultrasound probe of claim 13, wherein a thickness of the section of material is less than a thickness of the outer wall.

* * * * *